United States Patent
Stewart et al.

(10) Patent No.: US 8,604,276 B2
(45) Date of Patent: Dec. 10, 2013

(54) SWITCHGRASS UBIQUITIN PROMOTER (PVUBI2) AND USES THEREOF

(75) Inventors: C. Neal Stewart, Knoxville, TN (US); David George James Mann, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 433 days.

(21) Appl. No.: 12/797,248

(22) Filed: Jun. 9, 2010

(65) Prior Publication Data
US 2011/0023183 A1     Jan. 27, 2011

Related U.S. Application Data

(60) Provisional application No. 61/185,469, filed on Jun. 9, 2009.

(51) Int. Cl.
| | |
|---|---|
| *C12N 15/09* | (2006.01) |
| *C12N 15/11* | (2006.01) |
| *C12N 15/63* | (2006.01) |
| *C12N 15/82* | (2006.01) |
| *A01H 4/00* | (2006.01) |
| *A01H 5/00* | (2006.01) |
| *A01H 9/00* | (2006.01) |
| *C07K 14/415* | (2006.01) |
| *C07H 21/04* | (2006.01) |

(52) U.S. Cl.
USPC ........... 800/278; 800/279; 800/289; 800/292; 800/294; 800/298; 800/300; 800/302; 800/295; 536/24.1; 536/23.6; 435/419; 435/320.1; 435/468

(58) Field of Classification Search
None
See application file for complete search history.

(56) References Cited

U.S. PATENT DOCUMENTS

| | | | | |
|---|---|---|---|---|
| 6,528,701 | B1 * | 3/2003 | Wang et al. | 800/278 |
| 2011/0167514 | A1 * | 7/2011 | Brover et al. | 800/278 |

OTHER PUBLICATIONS

Kim Y, Buckley K, Costa MA, and An G. A 20 nucleoide upstream element is essential for the nopaline synthase (nos) promoter activity. Plant Molecular Biology. 1994. 24: 105-117.*

Binet, M. et al. "Structure and expression of sunflower ubiquitin genes," *Plant Molecular Biology*, 1991, pp. 395-407, vol. 17.

Burke, T.J. et al. "Characterization of a polyubiquitin gene from *Arabidopsis thaliana*," *Mol. Gen. Genet.*, 1988, pp. 435-443, vol. 213.

Christensen, A.H. et al. "Ubiquitin promoter-based vectors for high-level expression of selectable and/or screenable marker genes in monocotyledonous plants," *Transgenic Research*, 1996, pp. 213-218, vol. 5.

Christensen, A.H. et al. "Maize polyubiquitin genes: structure, thermal perturbation of expression and transcript splicing, and promoter activity following transfer to protoplasts by electroporation," *Plant Molecular Biology*, 1992, pp. 675-689, vol. 18.

Cornejo, M.-J. et al. "Activity of a maize ubiquitin promoter in transgenic rice," *Plant Molecular Biology*, 1993, pp. 567-581, vol. 23.

Garbarino, J.E. et al. "Isolation of a Polyubiquitin Promoter and Its Expression in Transgenic Potato Plants," *Plant Physiol.*, 1995, pp. 1371-1378, vol. 109.

Genschik, P. et al. "Structure and promoter activity of a stress and developmentally regulated polyubiquitin-encoding gene of *Nicotiana tabacum*," *Gene*, 1994, pp. 195-202, vol. 148.

Kawalleck, P. et al. "Polyubiquitin gene expression and structural properties of the *ubi*4-2 gene in *Petroselinum crispum*," *Plant Molecular Biology*, 1993, pp. 673-684, vol. 21.

Lescot, M. et al. "PlantCARE, a database of plant *cis*-acting regulatory elements and a portal to tools for in silico analysis of promoter sequences," *Nucleic Acids Research*, 2002, pp. 325-327, vol. 30, No. 1.

Tobias, C.M. et al. "Comparative Genomics in Switchgrass Using 61,585 High-Quality Expressed Sequence Tags," *The Plant Genome*, Nov. 2008, pp. 111-124, vol. 1, No. 2.

Wei, H. et al. "Comparative expression analysis of two sugarcane polyubiquitin promoters and flanking sequences in transgenic plants," *J. Plant Physiol.*, 2003, pp. 1241-1251, vol. 160.

* cited by examiner

*Primary Examiner* — Cathy Kingdon Worley
*Assistant Examiner* — Ashley K Buran
(74) *Attorney, Agent, or Firm* — Saliwanchik, Lloyd & Eisenchenk

(57) ABSTRACT

The subject application provides polynucleotides, compositions thereof and methods for regulating gene expression in a plant. Polynucleotides disclosed herein comprise novel sequences for a promoter isolated from *Panicum virgatum* (switchgrass) that initiates transcription of an operably linked nucleotide sequence. Thus, various embodiments of the invention comprise the nucleotide sequence of SEQ ID NO: 2 or fragments thereof comprising nucleotides 1 to 692 of SEQ ID NO: 2 that are capable of driving the expression of an operably linked nucleic acid sequence.

25 Claims, 19 Drawing Sheets
(6 of 19 Drawing Sheet(s) Filed in Color)

CCACTGGAGAGGGGCACACACGTCAGTGTTTGGTTTCCACTAGCACGAGTAGCGCAATCAGAAAATTTTCAATGCATGAAG
TACTAAACGAAGTTTATTTAGAAATTTTTTTAAGAAATGAGTGTAATTTTTTGCGACGAATTTAATGACAATAATTAATCG
ATGATTGCCTACAGTAATGCTACAGTAACCAACCTCTAATCATGCGTCGAATGCGTCATTAGATTCGTCTCGCAAAATAGC
ACAAGAATTATGAAATTAATTTTACAAACTATTTTTATTTAATACTAATAATTAACTGTCAAAGTTTGTGCTACTCGCAAG
AGTAGCGCGAACCAAACACGGCCTGGAGGAGCACGGTAACGGCGTCGACAAACTAACGGCCACCACCCGCCAACGCAAAGG
AGACGGATGAGAGTTGACTTCTTGACGGTTCTCCACCCCTCTGTCTCTCTGTCACTGGGCCCTGGGTCCCCCTCTCGAAAG
TTCCTCTGGCCGAAATTGCGCGGCGGAGACGAGGCGGGCGGAACCGTCACGGCAGAGGATTCCTTCCCCACCCTGCCTGGC
CCGGCCATATATAAACAGCCACCGCCCCTCCCCGTTCCCCATCGCGTCTCGTCTCGTGTTGTTCCCAGAACACAACCAAAA
TCCAAATCCTCCTCCTCCTCCCGAGCCTCGTCGATCCCTCACCCGCTTCAAGgtacggcgatcctcctctcccttctcccc
tcgatcgattatgcgtgttccgtttccgtttccgatcgagcgaatcgatggttaggacccatgggggacccatggggtgtc
gtgtggtggtctggtttgatccgcgatatttctccgttcgtagtgtagatctgatcgaatccctggtgaaatcgttgatcg
tgctattcgtgtgagggttcttaggtttggagttgtggaggtagttctgatcggtttgtaggtgagattttccccatgatt
ttgcttggctcgtttgtcttggttagattagatctgcccgcattttgttcgatatttctgatgcagatatgatgaataatt
tcgtccttgtatcccgcgtccgtatgtgtattaagtttgcaggtgctagttaggtttttcctactgatttgtcttatccat
tctgtttagcttgcaaggtttggtaatggtccggcatgtttgtctctatagattagagtagaataagattatctcaacaag
ctgttggcttatcaattttggatctgcatgtgtttcgcatctatatctttgcaattaagatggtagatggacatatgctcc
tgttgagttgatgttgtaccttttacctgaggtctgaggaacatgcatcctcctgctactttgtgcttatacagatcatca
agattatgcagctaatattcgatcagtttctagtatctacatggtaaacttgcatgcacttgctacttattttttgatatac
ttggatgataacatatgctgctggttgattcctacctacatgatgaacattttacaggccattagtgtctgtctgtatgtg
ttgttcctgtttgcttcagtctatttctgtttcattcctagtttattggttctctgctagatacttaccctgctgggctta
gttatcatcttatctcgaatgcattttcatgtttatagatgaatatacactcagataggtgtagatgtatgctactgtttc
tctacgttgctgtaggttttacctgtggcaactgcatactcctgttgcttcgctagatatgtatgtgcttatatagattaa
gatatgtgtgatggttctttagtatatctgatgatcatgtatgctcttttaacttcttgctacacttggtaacatgctgtg
atgctgtttgttgattctgtagcactaccaatgatgacccttatctctctttgtatatgatgtttctgtttgtttgaggctt
gtgttactgctagttacttaccctgttgcctggctaatcttctgcagATGCAGATCTTCGTTAAGACCCTCACCGGCAAGA
CCATCACCCTC

FIG. 3A

GAAGCCAACTAAACAAGACCATAACCATGGTGACATTTGACATAGTTGTTTACTACTTGCTTGAGCCCCACCCTTGCTTAT
CGGTTGAACATTACAAGATACACTGCGGGTGGCCTAAGGCACACCGTCCGAAACCGGCAAACCAAGCCTGATCGCCGAAAT
CCAAAATCACTACCGGCAATCTCTAAAGTTTATTTCATCCTTATATGACGAGGAAAGAAAAGAAGAGAGAAATAATATCTT
AACTTCTAAATCAGTCGCGTCAACTTTCTCGGCTAAGAAAGTGAGCACTATCATTTCGGAGACCATGTCATGAGTGCCGAC
TTGCCATATCTTATTATATTCTTATTTATTTAATTATAATCCCATTGCAATACGTCTATTCTATCATGGCCTGCCACTAAC
GCTCCGTCTAACGTCGTTAAGCCATTGTCATAAGCGGCTGCTCAAAACTCTTCCCGGTGGAGGCGAGGCGTTAACGGCGTC
TACAAATCTAACGGCCACCAACCATCCAGCCGCCTCTCGAAAGCTCCGCTCCGATCGCGGAAATTGCGTGGCGGAGACGAG
CGGGCTCCTCTCACACGGCCCGGAACCGTCACGGCACGGGTGGGGGATTCCTTCCCCAACCCTCCCCACCTCTCCTCCCCC
CGTCGCAGCCCATAAATACAGGGCCCTCCGCGCCTCTTCCCACAATCTCACATCGTCTCATCGTTCGGAGCGCACAACCCC
CGGGTTCCAAATCCAAATTGCTCTTCTCGCGACCCTCGGCGATCCTTCCCCCGCTTCAAGgtacggcgatcgtctcccccg
tcctcttgccccatctcctcgctcggcgtggtttggtggttctgcttggtctgtggctaggaactaggctgaggcgttgac
gaaatcatgctagatccgcgtgtttcctgatcgtgggtggctgggaggtggggttttcgtgtagatctgatcggttccgct
gtttatcctgtcatgctcatgtgatttgtggggattttaggtcgtttgtccgggaatcgtggggttgcttctaggctgttc
gtagatgagatcgttctcacgatctgctgggtcgctgcctaggttcagctaggtctgccctgttttttgggttcgttttcgg
gatctgtacgtgcatctattatctggttcgatggtgctagctaggaacaaacaactgattcgtccgatcgattgttttgtt
gccatgtgcaaggttaggtcgttatctgattgctgtagatcagagtagaataagatcatcacaagctagctcttgggctta
ttatgaatctgcgtttgttgcatgattaagatgattatgcttttttcttatgctgccgtttgtatatgatgcggtagctttt
aactgaatagcacacctttcctgtttagttagattagattagattgcatgatagatgaggatatatgctgctacatcagtt
tgatgattctctggtacctcataatcaactagctcatgtgcttaaattgaaactgcatgtgccacatgattaagatgctaa
gattggtgaagatatatacgctgctgttcctataggatcctgtagcttttacctggtcaacatgcatcgtcctgttatgga
tagatatgcatgatagatgaagatatgtactgctacaatttgatgattcttttgtgcacctgatgatcatgcatgctcttt
gcccttactttgatatacttggatgatggcatgcttagtactaatgatgtgatgaacacacatgacctgttggtatgaata
tgatgttgctgtttgcttgtgatgagttctgttttgtttactgctaggcacttaccctgttgtctggttctcttttgcag<u>AT
GCAGATCTTTGTGAAGACCCTCACCGGCAAGACCATCACCCTC</u>

FIG. 3B

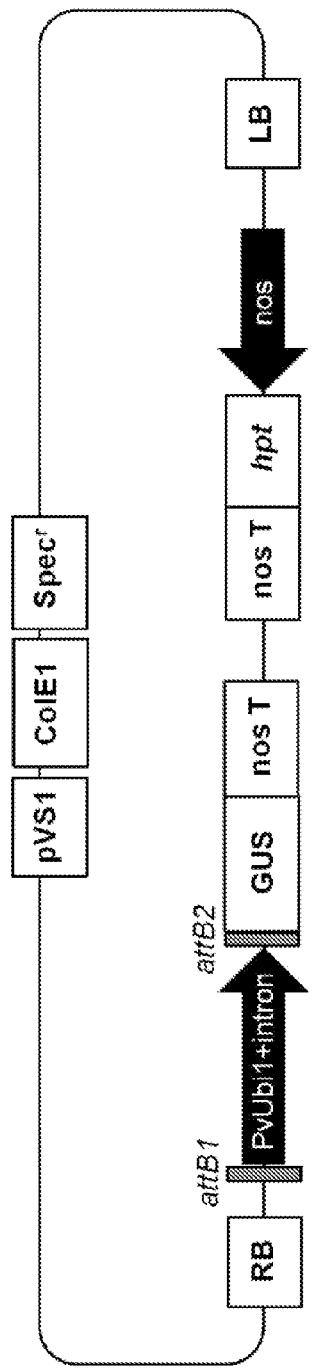
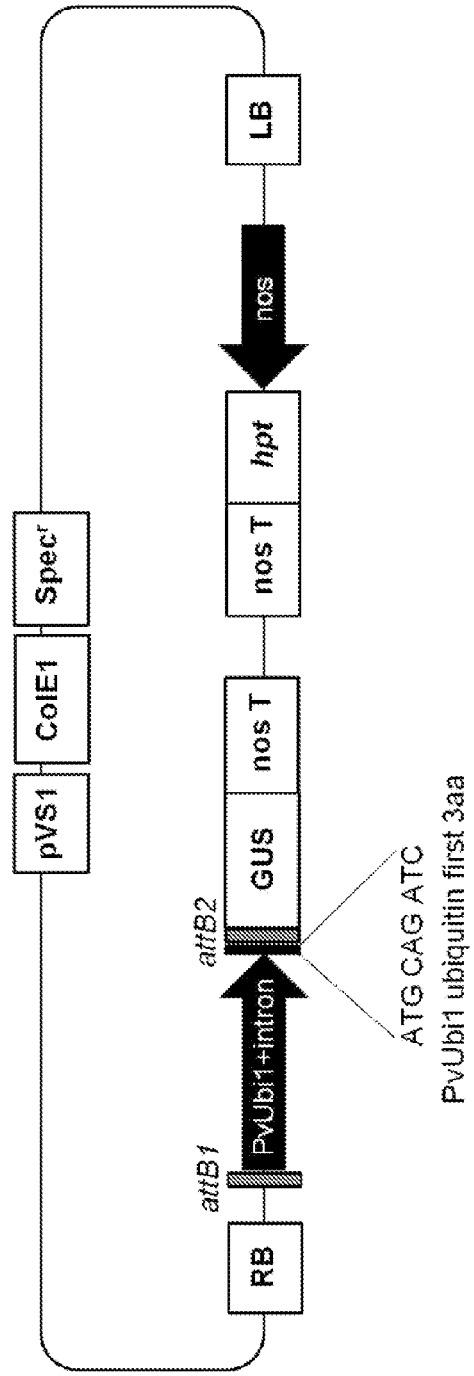
FIG. 4A
FIG. 4B

```
CCACTGGAGAGGGGCACACACGTCAGTGTTTGGTTTCCACTAGCACGAGTAGCGCAATCAGAAAATTTTCAATGCAT
-607             -589  -584     -577  -572                      -553 -550           -538  -535
GAAGTACTAAACGAAGTTTATTTAGAAATTTTTTTAAGAAATGAGTGTAATTTTTTGCGACGAATTTAATGACAATA
                                                                              -458 -455
ATTAATCGATGATTGCCTACAGTAATGCTACAGTAACCAACCTCTAATCATGCGTCGAATGCGTCATTAGATTCGTC
                                                               -332    -380
                                                              -391   -387
TCGCAAAATAGCACAAGAATTATGAAATTAATTTTACAAACTATTTTTATTTAATACTAATAATTAACTGTCAAAGT
                  -350         -339                                -312   -307
TTGTGCTACTCGCAAGAGTAGCGCGAACCAAACACGGCCTGGAGGAGCACGGTAACGGCGTCGACAAACTAACGGCC

ACCACCCGCCAACGCAAAGGAGACGGATGAGAGTTGACTTCTTGACGGTTCTCCACCCCTCTGTCTCTCTGTCACTG
-221   -216                                                 -170   -165
GGCCCTGGGTCCCCCTCTCGAAAGTTCCTCTGGCCGAAATTGCGCGGCGGAGACGAGGCGGGCGGAACCGTCACGGC
                                 -112   -107                                  -77  -73
                                                                              +1
AGAGGATTCCTTCCCCACCCTGCCTGGCCCGGCCATATATAAACAGCCACCGCCCCTCCCCGTTCCCCATCGCGTCT
          -54  -49             -33   -26
CGTCTCGTGTTGTTCCCAGAACACAACCAAAATCCAAATCCTCCTCCTCCTCCCGAGCCTCGTCGATCCCTCACCCG

CTTCAAG/gtacggcgatcctcctctcccttctcccctcgatcgattatgcgtgttccgtttccgtttccgatcgag cgaatcgatggttaggacccatgggggacccatggggtgtcgtgtggtggtctggtttgatccgcgatatttctccg ttcgtagtgtagatctgatcgaatccctggtgaaatcgttgatcgtgctattcgtgtgagggttcttaggtttggag ttgtggaggtagttctgatcggtttgtaggtgagattttccccatgattttgcttggctcgtttgtcttggttagat tagatctgcccgcatttgttcgatatttctgatgcagatatgatgaataatttcgtccttgtatcccgcgtccgta tgtgtattaagtttgcaggtgctagttaggttttttcctactgatttgtcttatccattctgtttagcttgcaaggtt tggtaatggtccggcatgtttgtctctatagattagagtagaataagattatctcaacaagctgttggcttatcaat tttggatctgcatgtgtttcgcatctatatctttgcaattaagatggtagatggacatatgctcctgttgagttgat gttgtaccttttacctgaggtctgaggaacatgcatcctcctgctactttgtgcttatacagatcatcaagattatg cagctaatattcgatcagtttctagtatctacatggtaaacttgcatgcacttgctacttattttttgatatacttgg atgataacatatgctgctggttgattcctacctacatgatgaacattttacaggccattagtgtctgtctgtatgtg ttgttcctgtttgcttcagtctatttctgtttcattcctagtttattggttctctgctagatacttaccctgctggg cttagttatcatcttatctcgaatgcattttcatgtttatagatgaatatacactcagataggtgtagatgtatgct actgtttctctacgttgctgtaggtttttacctgtggcaactgcatactcctgttgcttcgctagatatgtatgtgct tatatagattaagatatgtgtgatggttctttagtatatctgatgatcatgtatgctctttttaacttcttgctacac ttggtaacatgctgtgatgctgtttgttgattctgtagcactaccaatgatgaccttatctctctttgtatatgatg tttctgtttgtttgaggcttgtgttactgctagttacttaccctgttgcctggctaatcttctgcag/ATG CAG
                                                                    Met Gln
ATC TTC GTT AAG ACC CTC ACC GGC AAG ACC ATC ACC CTC
Ile Phe Val Lys Thr Leu Thr Gly Lys Thr Ile Thr Leu
```

FIG. 8A

```
GAAGCCAACTAAACAAGACCATAACCATGGTGACATTTGACATAGTTGTTTACTACTTGCTTGAGCCCCACCCTTGC
-602                                                              -625   -620
TTATCGGTTGAACATTACAAGATACACTGCGGGTGGCCTAAGGCACACCGTCCGAAACCGGCAAACCAAGCCTGATC
                                           -568  -563
                                              -564  -559
GCCGAAATCCAAAATCACTACCGGCAATCTCTAAAGTTTATTTCATCCTTATATGACGAGGAAAGAAAAGAAGAGAG
                        -514 -511
AAATAATATCTTAACTTCTAAATCAGTCGCGTCAACTTTCTCGGCTAAGAAAGTGAGCACTATCATTTCGGAGACCA
                          -432   -428
TGTCATGAGTGCCGACTTGCCATATCTTATTATATTCTTATTTATTTAATTATAATCCCATTGCAATACGTCTATTC
-383   -379                                                       -321  -318
TATCATGGCCTGCCACTAACGCTCCGTCTAACGTCGTTAAGCCATTGTCATAAGCGGCTGCTCAAAACTCTTCCCGG
           -296   -291                         -261  -257
TGGAGGCGAGGCGTTAACGGCGTCTACAAATCTAACGGCCACCAACCATCCAGCCGCCTCTCGAAAGCTCCGCTCCG
ATCGCGGAAATTGCGTGGCGGAGACGAGCGGGCTCCTCTCACACGGCCCGGAACCGTCACGGCACGGGTGGGGGATT
                                                    -99   -95                +1
CCTTCCCCAACCCTCCCCACCTCTCCTCCCCCCGTCGCAGCCCATAAATACAGGGCCCTCCGCGCCTCTTCCCACAA
                           -48  -43        -32  -27
TCTCACATCGTCTCATCGTTCGGAGCGCACAACCCCCGGGTTCCAAATCCAAATTGCTCTTCTCGCGACCCTCGGCG
ATCCTTCCCCCGCTTCAAG/gtacggcgatcgtctcccccgtcctcttgccccatctcctcgctcggcgtggtttgg
tggttctgcttggtctgtggctaggaactaggctgaggcgttgacgaaatcatgctagatccgcgtgtttcctgatc
gtgggtggctgggaggtggggttttcgtgtagatctgatcggttccgctgtttatcctgtcatgctcatgtgatttg
tggggattttaggtcgtttgtccgggaatcgtggggttgcttctaggctgttcgtagatgagatcgttctcacgatc
tgctgggtcgctgcctaggttcagctaggtctgccctgttttgggttcgttttcgggatctgtacgtgcatctatt
atctggttcgatggtgctagctaggaacaaacaactgattcgtccgatcgattgttttgttgccatgtgcaaggtta
ggtcgttatctgattgctgtagatcagagtagaataagatcatcacaagctagctcttgggcttattatgaatctgc
gtttgttgcatgattaagatgattatgcttttcttatgctgccgtttgtatatgatgcggtagcttttaactgaat
agcacacctttcctgtttagttagattagattagattgcatgatagatgaggatatatgctgctacatcagtttgat
gattctctggtacctcataatcaactagctcatgtgcttaaattgaaactgcatgtgccacatgattaagatgctaa
gattggtgaagatatatacgctgctgttcctataggatcctgtagcttttacctggtcaacatgcatcgtcctgtta
tggatagatatgcatgatagatgaagatatgtactgctacaatttgatgattcttttgtgcacctgatgatcatgca
tgctctttgcccttactttgatatacttggatgatggcatgcttagtactaatgatgtgatgaacacacatgacctg
ttggtatgaatatgatgttgctgtttgcttgtgatgagttctgtttgtttactgctaggcacttaccctgttgtctg
gttctcttttgcag/ATG CAG ATC TTT GTG AAG ACC CTC ACC GGC AAG ACC ATC ACC CTC
               Met Gln Ile Phe Val Lys Thr Leu Thr Gly Lys Thr Ile Thr Leu
```

17d 17d
following
heat shock
treatment

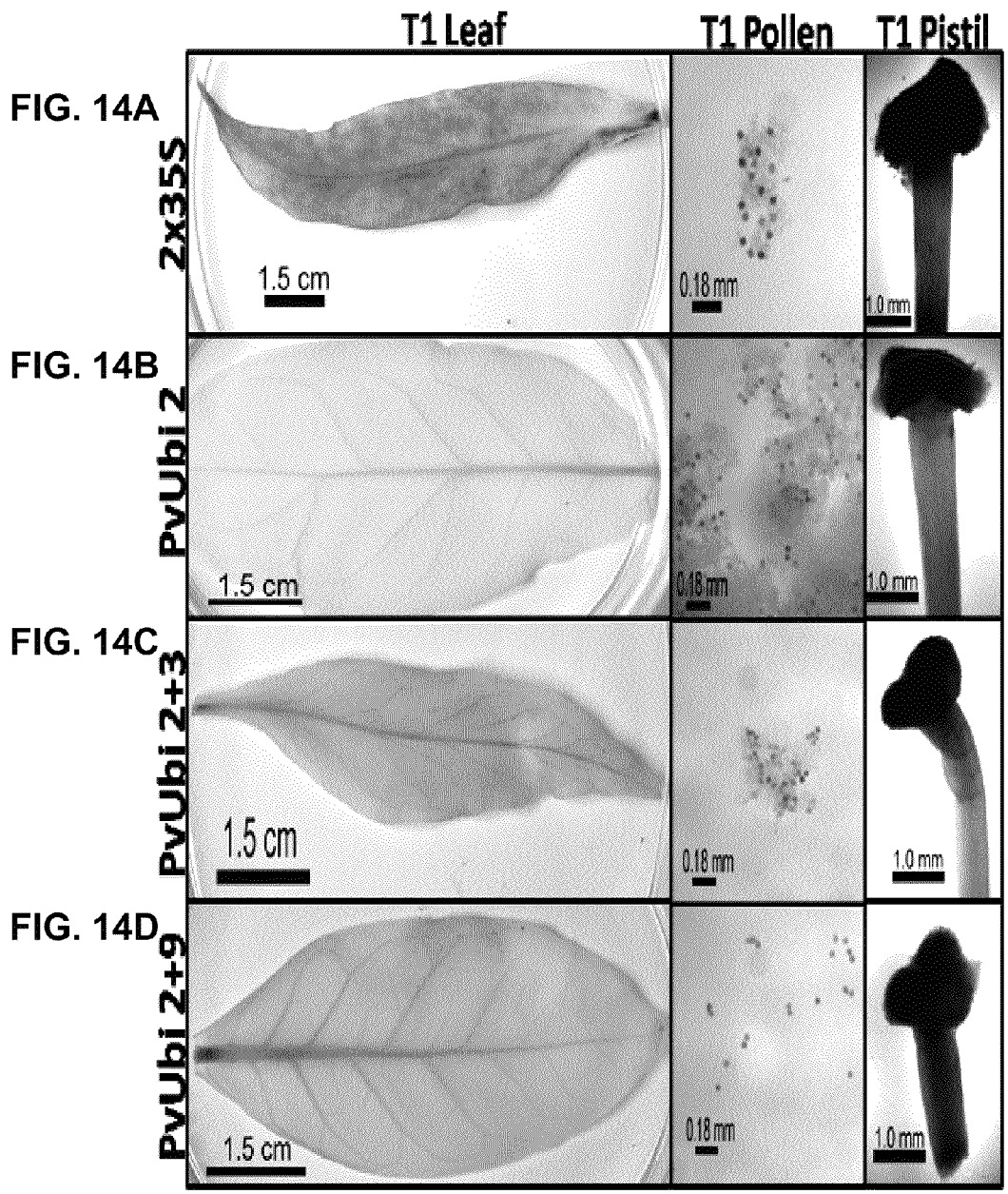

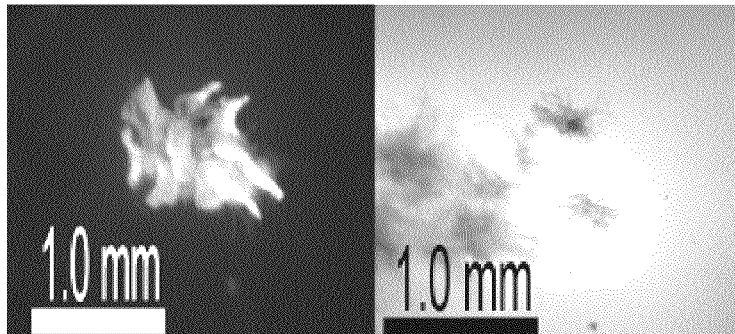
FIG. 15A  FIG. 15E
FIG. 15B  FIG. 15F
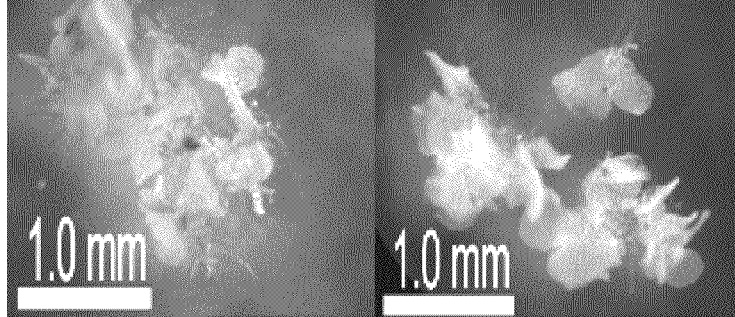
FIG. 15C  FIG. 15G
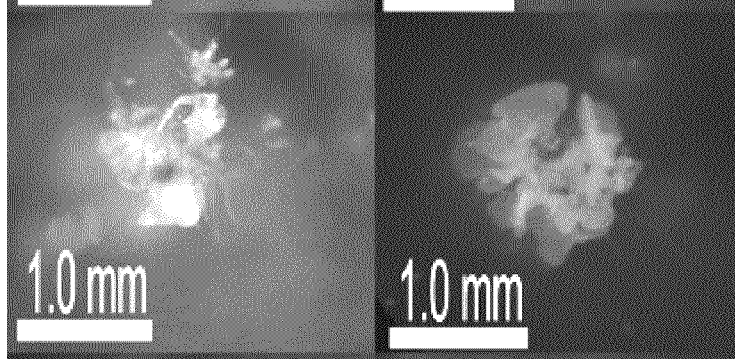
FIG. 15D  FIG. 15H
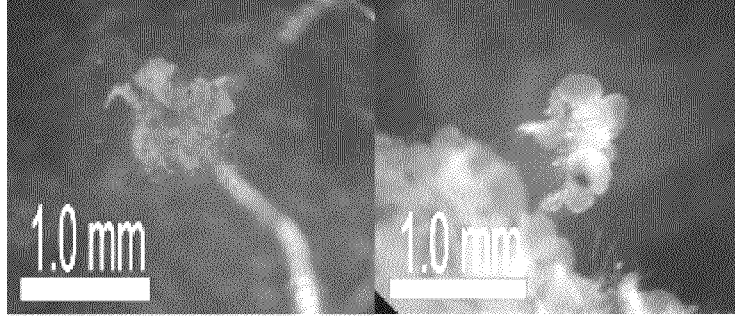

ial Application Ser. No. 61/185,469, filed Jun. 9, 2009, the disclosure of which is hereby incorporated by reference in its entirety, including all figures, tables and amino acid or nucleic acid sequences.

This invention was made with United States Government support under Department of Energy Bioenergy Science Center IP Management Plan Agreement contract number DE-AC05-00OR22725. Subcontract No. UT-4000063906. The United States Government has certain rights in the invention.

BACKGROUND OF THE INVENTION

Recent advances in plant genetic engineering have enabled the engineering of plants having improved characteristics or traits, such as disease resistance, insect resistance, herbicide resistance, enhanced stability or shelf-life of the ultimate consumer product obtained from the plants and improvement of the nutritional quality of the edible portions of the plant. Thus, one or more desired genes from a source different than the plant, but engineered to impart different or improved characteristics or qualities, can be incorporated into the plant's genome. One or more new genes can then be expressed in the plant cell to exhibit the desired phenotype such as a new trait or characteristic.

SUMMARY OF THE INVENTION

The subject application provides polynucleotides, compositions thereof and methods for regulating gene expression in a plant. Polynucleotides disclosed herein comprise novel sequences for a promoter that initiates transcription of an operably linked nucleotide sequence. Thus, various embodiments of the invention comprise the nucleotide sequence of SEQ ID NO: 1 or 2 or fragments thereof that are capable of driving the expression of an operably linked nucleic acid sequence. Other polynucleotides disclosed herein provide nucleotide sequences having at least 70% sequence identity to the sequence set forth in SEQ ID NO: 1 or 2 or fragments thereof that are capable of driving the expression of an operably linked nucleic acid sequence. Polynucleotides complementary to such polynucleotides (polynucleotide sequences having at least 70% sequence identity to SEQ ID NO: 1, 2 or fragments thereof) are also provided by the subject application.

Additionally, DNA constructs (sometimes referred to as nucleotide constructs) comprising a promoter, as disclosed herein, operably linked to a heterologous nucleotide sequence of interest wherein said promoter is capable of driving expression of the operably linked heterologous nucleotide sequence in a plant cell are provided. Further aspects of the invention provide expression vectors and plants, seed, gametophytes, spores, zygotes or plant cells having stably incorporated into their genomes a DNA construct as disclosed herein.

Methods of expressing a chosen nucleotide sequence in a plant, comprising transforming a plant cell with a DNA construct, as disclosed herein, and optionally regenerating a transformed plant from said plant cell are also provided. The DNA construct comprises a promoter and a heterologous nucleotide sequence operably linked to said promoter, wherein said promoter initiates transcription of said nucleotide sequence in a plant cell. Thus, the promoter disclosed herein is useful for controlling the expression of operably linked coding sequences.

Downstream from and under the transcriptional initiation regulation of the promoter will be a sequence of interest that will provide for modification of the phenotype of the plant. Such modification caused by the sequence of interest includes modulating the production of an endogenous product, as to amount or relative distribution or the production of an exogenous expression product, to provide for a novel function or product in the plant. For example, a heterologous nucleotide sequence that encodes a gene product that confers pathogen, herbicide, salt, cold, drought, or insect resistance can be operably linked to a promoter as disclosed herein.

In a further aspect of the invention, methods for modulating expression of a gene product in a stably transformed plant comprising the steps of (a) transforming a plant cell with a DNA construct comprising the disclosed promoter or fragments thereof that are capable of driving the expression of an operably linked nucleic acid sequence operably linked to at least one nucleotide sequence; (b) growing the plant cell and (c) regenerating a stably transformed plant from the plant cell wherein the expression of the operably linked nucleotide sequence alters the phenotype of the plant.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 3A-3B. Nucleotide sequences of the 5' upstream regions of PvUbi1 (3A, SEQ ID NO: 1) and PvUbi2 (3B, SEQ ID NO: 2). The putative TATA box is underlined and the intron is shown in lowercase. The first 45 nucleotides of ubiquitin coding region are also shown and indicated by double underlining.

FIGS. 4A-4C. Schematic illustrations of the constructs containing PvUbi1 promoter and intron (4A), PvUbi1 promoter, intron and 3aa fusion (4B, SEQ ID NO: 45). and PvUbi1 promoter, intron and 9aa fusion (4C. SEQ ID NO: 44) variations in the pGWB533 backbone. Abbreviations: PvUbi1 (Switchgrass ubiquitin 1 promoter and intron), nos (*A. tumefaciens nos* promoter), hpt (hygromycin resistance gene), attB1 and attB2 ( ) nos T (*A. tumefaciens nos* terminator sequence), LB (left border), RB (right border), ColE1 (contains the origin of replication and basis of mobility in *E. coli*), pVS1 (origin of replication in *A. tumefaciens*), Spec$^r$ (spectinomycin bacterial resistance).

SWITCHGRASS UBIQUITIN PROMOTER (PVUBI2) AND USES THEREOF

CROSS-REFERENCE TO RELATED APPLICATION

This application claims the benefit of U.S. Provision

Figure 7:
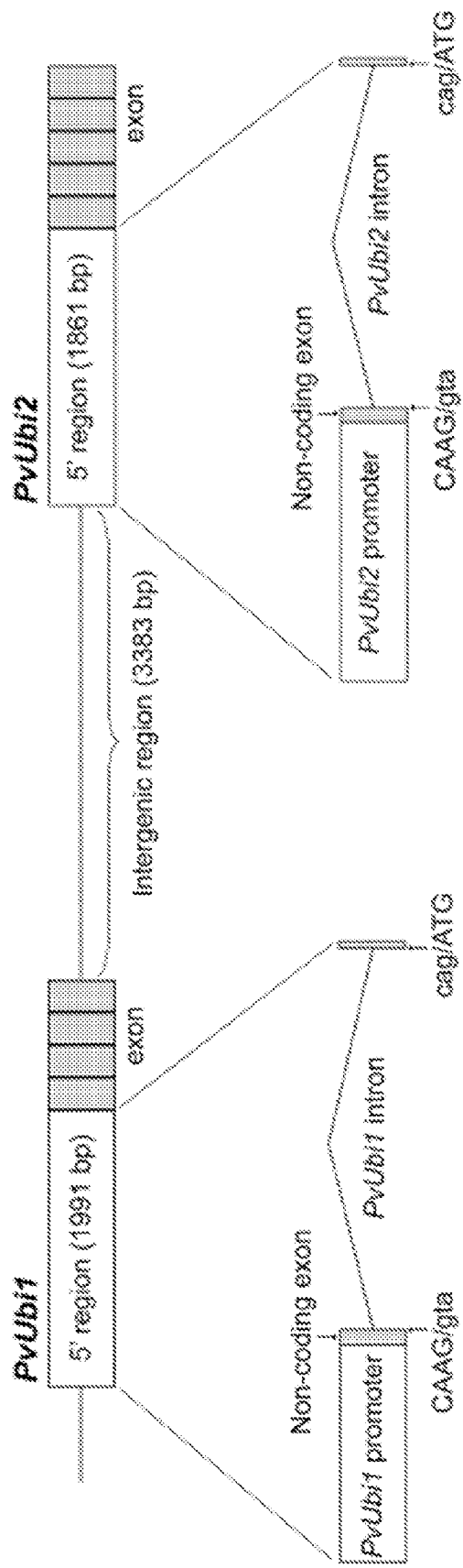

FIG. 7. The structural map and organization of the PvUbi1 and PvUbi2 genes within the 10.4 kilobase (kb) switchgrass genomic contig Pv9G7B5 sequence. The light gray boxes represent the 228 base pair ubiquitin monomer repeats of the translated exon. The black boxes represent the non-coding exons down stream of each TATA box for PvUbi1 and PvUbi2. The intron splices sites (CAAG/gta and cag/ATG) are also shown.

FIGS. 8A-8B. The sequences of the promoter regions for PvUbi1 (SEQ ID NO: 1; FIG. 8A) and PvUbi2 (SEQ ID NO: 2; FIG. 8B). These include potential regulatory elements (underlined). The putative TATA boxes are double underlined and the transcriptional initiation site is designated as +1. Uppercase letters represent the 5' putative promoter region containing regulatory elements; upper case italic letters represent the 5' untranslated sequence of the non-coding exon; lower case letters represent the intron sequence; upper case italic bold letters represent the exon with the corresponding amino acid displayed beneath each codon (SEQ ID NO: 3). The forward slashes represent the boundary between the exon and intron with the intron splice sites shown in bold.

Figure 9:
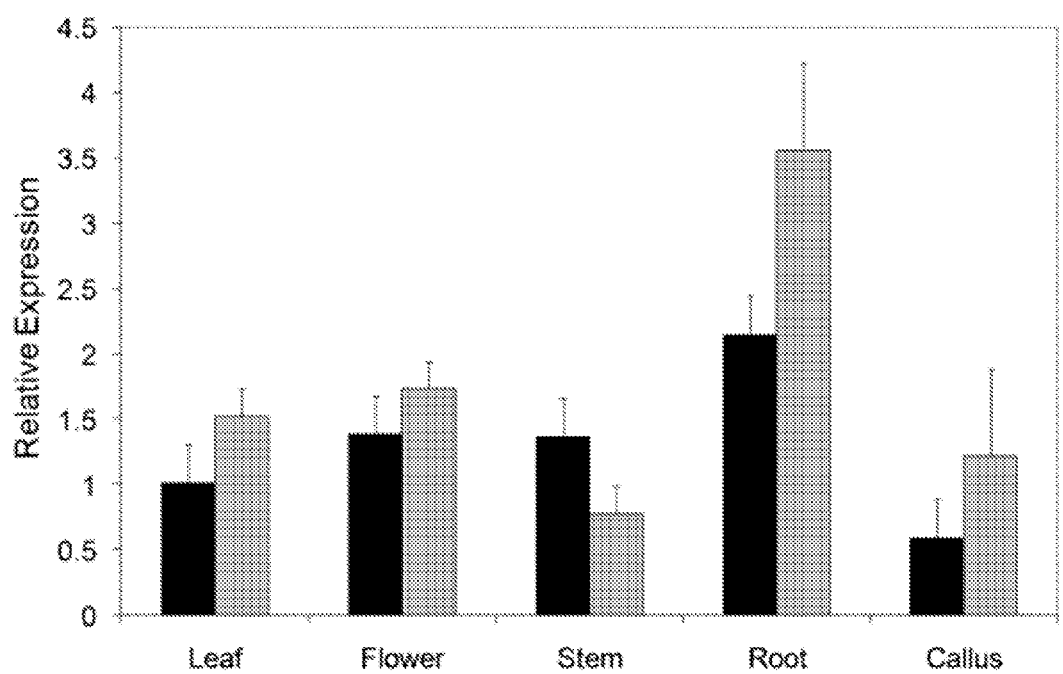

FIG. 9. Expression analysis of switchgrass Pvubi-1 (black) and Pvubi-2 (gray) in a variety of switchgrass tissues using qRT-PCR. Relative quantification was performed using the standard curve method, and transcript accumulation of each gene was normalized to the quantity of expressed switchgrass actin gene (PvAct). Each bar represents the mean of three independent biological experiments with the standard errors of the noted mean.

Figure 10:
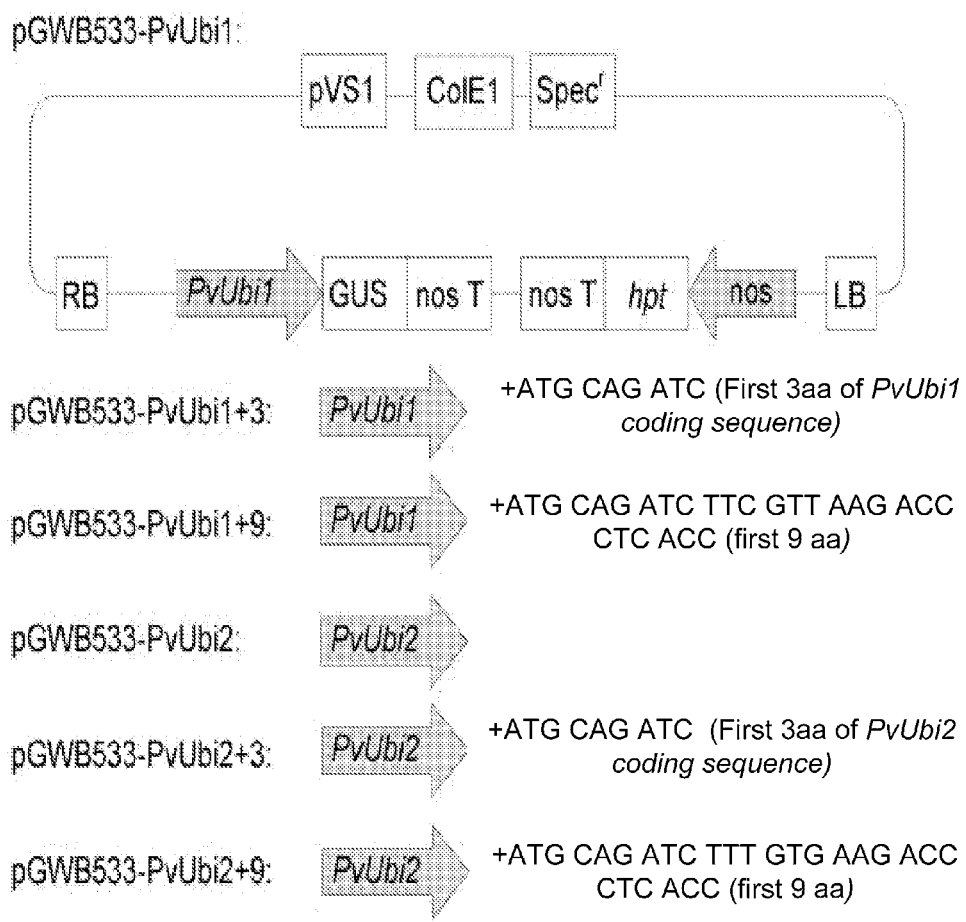

FIG. 10. Schematic diagrams of the GUS expression constructs containing PvUbi1 and PvUbi2 with the pGWB533 DNA backbone (Nakagawa et al. 2007). Promoters driving GUS expression are shown in gray. The PvUbi1 and PvUbi2 promoters shown each contain their respective promoter regions, 5' UTR non-coding exons and introns. Additionally, the first three (PvUbi1 +3 and PvUbi2+3, SEQ ID NO: 45) or nine (PvUbi1 +9 (SEQ ID NO: 46) and PvUbi2+9 (SEQ ID NO: 47)) amino acids have been fused to the 3' end of the intron. Abbreviations: PvUbi1 (switchgrass polyubiquitin 1 promoter and intron), GUS (uidA gene encoding for β-glucuronidase), hpt (hygromycin resistance gene), nos T (*A. tumefaciens* nos terminator sequence), LB (leftborder), RB (rightborder), ColE1 (origin of replication in *E.coli*), PVS1 (origin of replication in *A. tumefaciens*), Spec$^r$ (spectinomycin bacterial resistance).

Figures 11A, 11B, 11C, 11D:
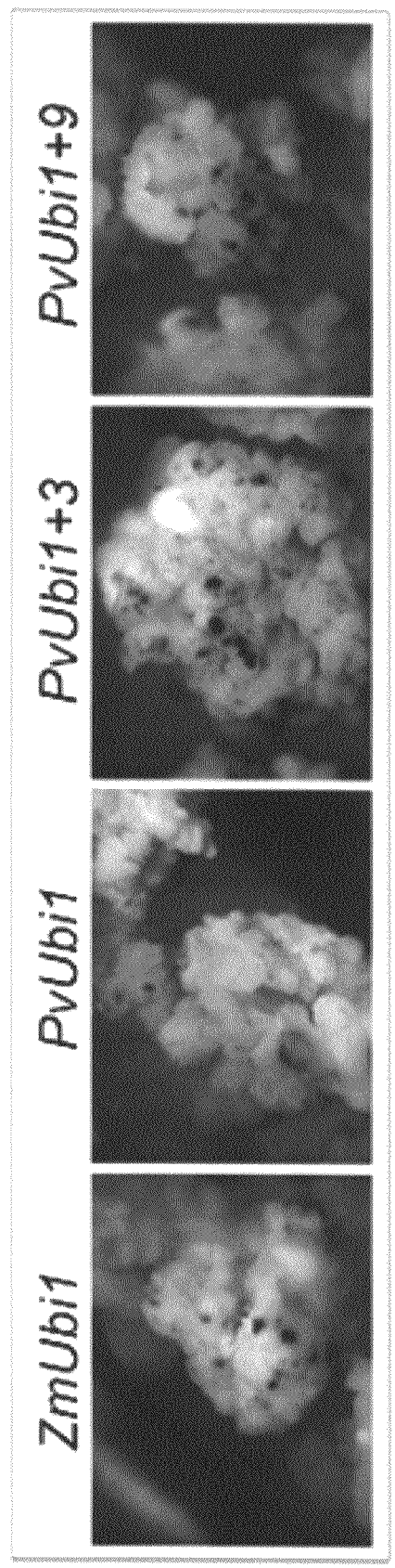

FIGS. 11A-11D. Representative images of switchgrass callus after histochemical staining following particle bombardment with constructs containing GUS under the control of ZmUbi1 (pAHC25; FIG. 11A), PvUbi1 (pGWB533-PvUbi1; FIG. 11B), PvUbi1+3 (pGWB533-PvUbi1+3; FIG. 11C) and PvUbi1+9 (pGWB533-PvUbi1+9; FIG. 11D).

Figure 12A:
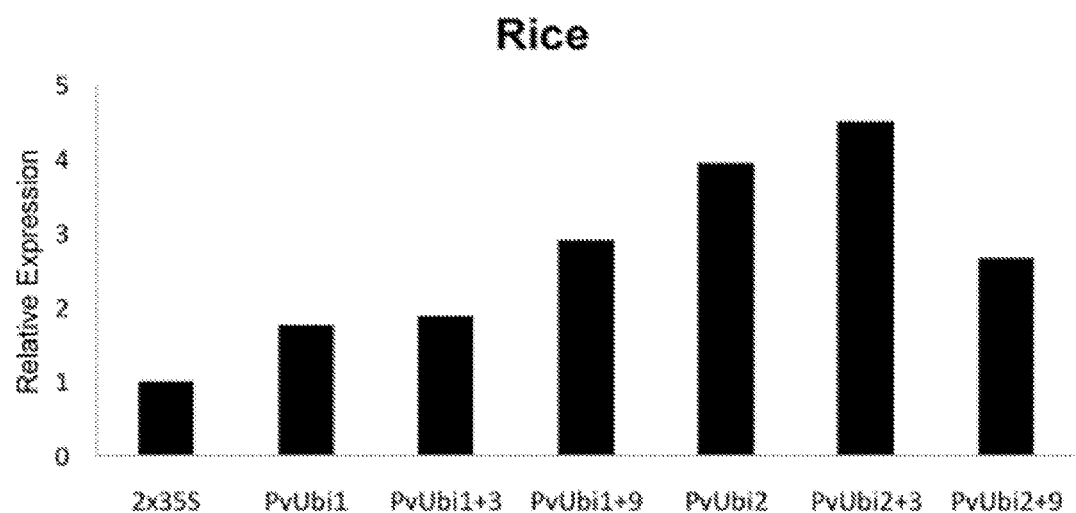
Figure 12B:
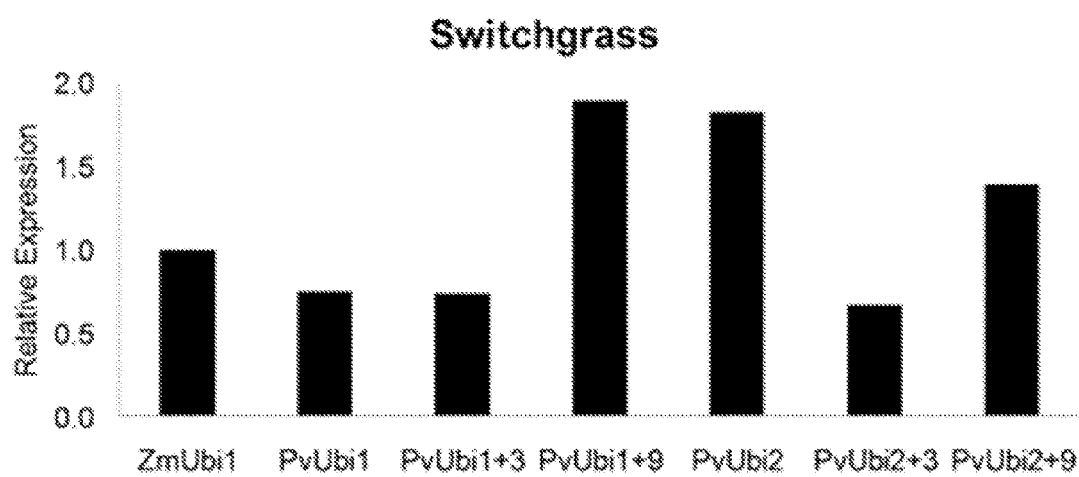
Figure 12C:
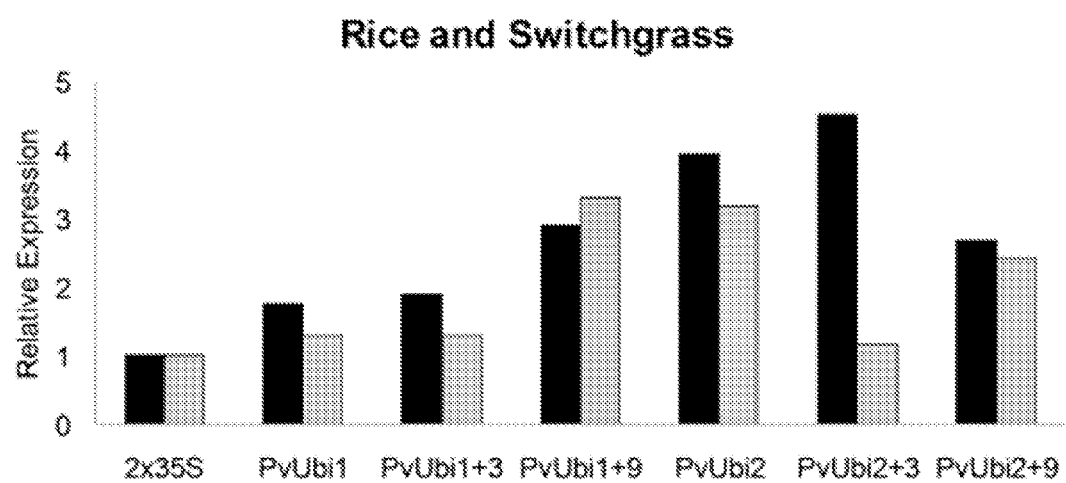

FIGS. 12A-12C. Comparison of the relative transient expression of GUS under the control of different PvUbi1 and PvUbi2 promoter variants in rice (FIG. 12A) and switchgrass (FIG. 12B). Each promoter construct contained the same pGWB533 DNA backbone, including the ZmUbi1 (in switchgrass) and the 2x35S (in rice) promoters used as positive controls. Relative GUS expression levels were also normalized to the same positive control (pGWB533-2x35S) to evaluate a direct comparison of the PvUbi1 and PvUbi2 promoter variants in rice and switchgrass (FIG. 12C). The pGWB535-ZmUbi1 containing the luciferase coding region served as an internal control in co-bombardment and MUG to LUC ratios were calculated for two independent experiments and three replicates (see Materials and Methods). The relative expression levels of GUS under the control of ZmUbi1 (a) and 2x35S (b) were set to 1, a dimensionless value. All other promoter values are shown relative to these controls.

Figures 13A, 13B, 13C:
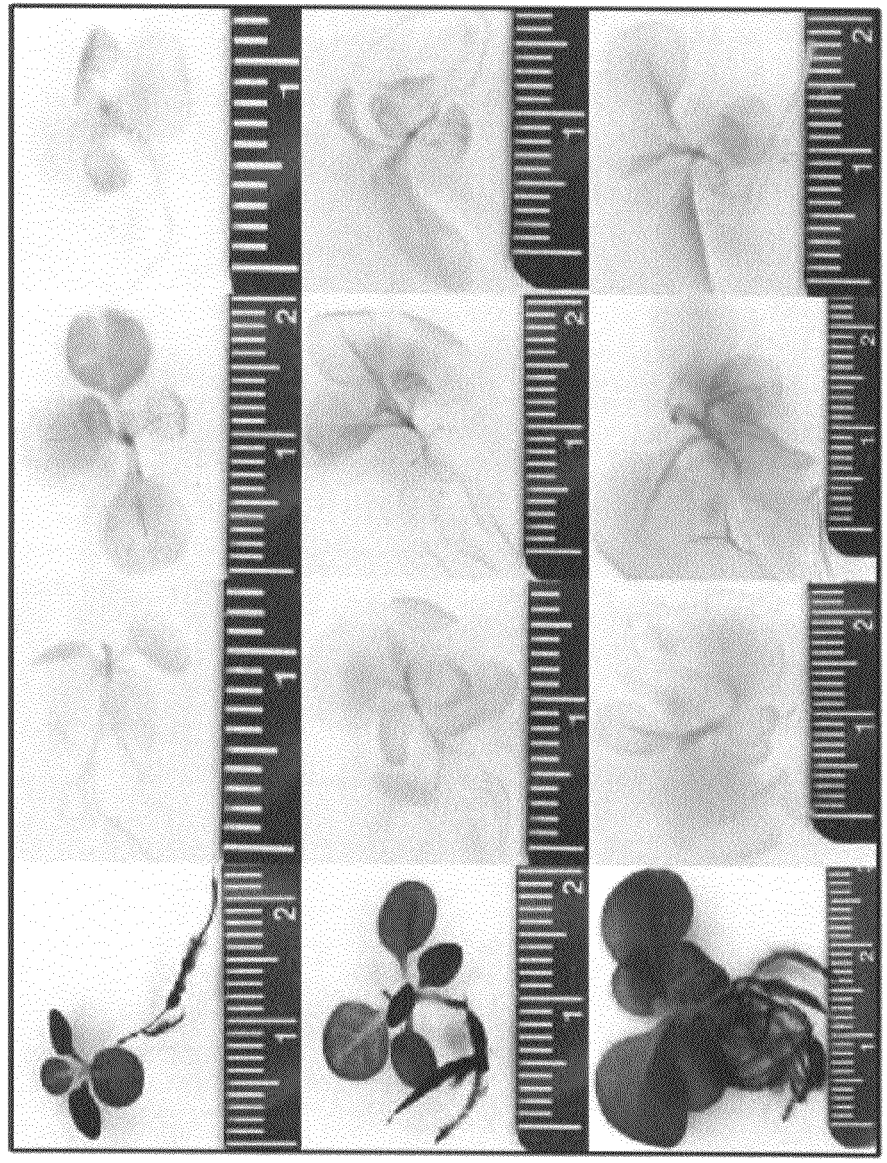

FIGS. 13A-13C. Histochemical staining of GUS expression in tobacco seedlings driven by the dual CaMV 35S (2x35S) promoter (positive control) and the PvUbi2 promoter variants (PvUbi2, PvUbi2+3, PvUbi2+9). PvUbi2+3 and PvUbi2+9 showed the strongest expression over the time course of staining. Staining was performed at 10 (10*d*; FIG. 13A) and 17 days (17*d*; FIG. 13B) post-germination. Heat shock induction of seedlings was performed at 42° C. for 1 hour followed directly by histochemical staining (FIG. 13C).

FIGS. 14A-14D. Histochemical staining of GUS expression in the leaves, pollen and pistils of mature tobacco plants driven by the dual CaMV 35S (2x35S; FIG. 14A) promoter (positive control) and the PvUbi2 promoter variants (PvUbi2; FIG. 14B, PvUbi2+3; FIG. 14C, PvUbi2+9; FIG. 14D). GUS expression was observed for all PvUbi2 promoter variants in leaves, pollen and pistil, while PvUbi2+3 showed the strongest levels of expression. In leaves, expression was specific to the vascular tissue.

FIGS. 15A-15H. Representative images of *Pteris vittata* gametophytes after histochemical staining following particle bombardment with constructs containing GUS under the control of 2x35S (pGWB533-2x35S), PvUbi1 (pGWB533-PvUbi1), PvUbi1+3 (pGWB533-PvUbi1+3) and PvUbi1+9 (pGWB533-PvUbi1+9; FIGS. 15A-D) and with constructs containing GUS under the control of 2x35S (pGWB533-2x35S), PvUbi2 (pGWB533-PvUbi2), PvUbi2+3 (pGWB533-PvUbi2+3) and PvUbi2+9 (pGWB533-PvUbi2+9; FIGS. 15E-H).

Figure 16:
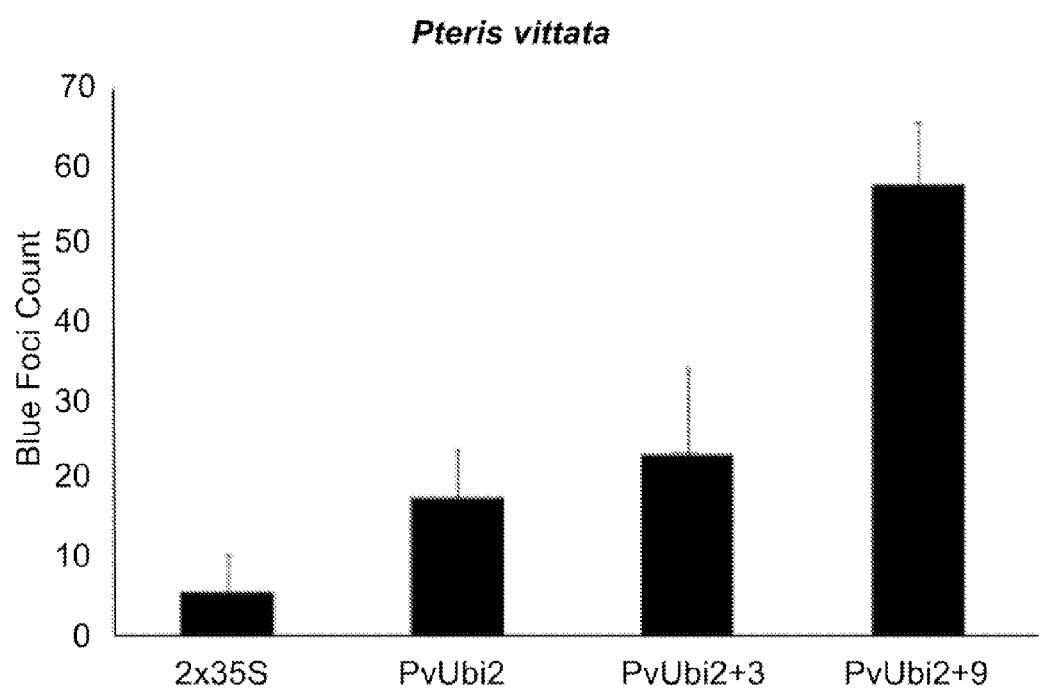

FIG. 16. Transient GUS expression under the control of 2x35S, PvUbi2, PvUbi2+3 and PvUbi2+9 promoters in *Pteris vittata* gametophytes measured by counting blue foci following histochemical staining. Each bar represents the mean of two biological replicates with the standard deviations of the noted mean.

DETAILED DESCRIPTION OF THE INVENTION

The subject invention also provides isolated, recombinant, and/or purified polynucleotide sequences comprising:
  a) a polynucleotide sequence comprising:
    i) SEQ ID NO: 1 (PvUbi1) or fragments thereof that are capable of driving the expression of an operably linked nucleic acid sequence;
    ii) SEQ ID NO: 2 (PvUbi2) or fragments thereof that are capable of driving the expression of an operably linked nucleic acid sequence;
  b) a polynucleotide sequence having at least about 70% to 99.99% identity to a polynucleotide sequence set forth in (a) capable of driving the expression of an operably linked nucleic acid sequence;
  c) a polynucleotide that is fully complementary to the polynucleotides set forth in (a) or (b);
  d) a DNA construct comprising a polynucleotide sequence as set forth in (a) or (b) operably linked to a heterologous nucleotide (polynucleotide) sequence;
  e) a host cell comprising a construct as set forth in (d);
  f) a polynucleotide that hybridizes under low, intermediate or high stringency with a polynucleotide sequence as set forth in (a), (b) or (c); or
  g) a probe comprising a polynucleotide according to (a), (b) or (c) and, optionally, a label or marker.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

A homologous polynucleotide or polypeptide sequence, for the purposes of the present invention, encompasses a sequence having a percentage identity with the polynucleotide or polypeptide sequences, set forth herein, of between at least (or at least about) 20.00% to 99.99% (inclusive). The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection. In certain aspects of the invention, homologous sequences to SEQ ID NO: 1 or SEQ ID NO: 2 have at least 70% sequence identity to SEQ ID NO: 1 or SEQ ID NO: 2 over its full length (or over the full length of a given fragment of SEQ ID NO: 1 or 2).

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence". In various aspects of the invention, sequences are "fully complementary" to a reference sequence (e.g., SEQ ID NO: 1). The phrase "fully complementary" refers to sequences contain no mismatches in their base pairing.

Sequence homology and sequence identity can also be determined by hybridization studies under high stringency, intermediate stringency, and/or low stringency. Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$Tm=81.5°$ C.$+16.6$ Log$[Na^+]+0.41$(% G+C)$-0.61$(% formamide)$-600$/length of duplex in base pairs.

Washes are typically carried out as follows:

(1) twice at room temperature for 15 minutes in 1×SSPE, 0.1% SDS (low stringency wash);

(2) once at $T_m-20°$ C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5× Denhardt's solution, 0.1% SDS, 0.1 mg/ml denatured DNA. $T_m$ for oligonucleotide probes can be determined by the following formula:

$T_m$(° C.)$=2$(number T/A base pairs)$^+4$(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

Low: 1 or 2×SSPE, room temperature
Low: 1 or 2×SSPE, 42° C.
Intermediate: 0.2× or 1×SSPE, 65° C.
High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 μg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J Biol. Chem.* 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments is the total number of nucleotides found in the full-length sequence of SEQ ID NO: 1 or 2, optionally less the ubiquitin monomer sequence as identified in FIG. 3). The term "successive" can be interchanged with the term "consecutive" or the phrase "contiguous span". Thus, in some embodiments, a polynucleotide fragment may be referred to as "a contiguous span of at least X nucleotides, wherein X is any integer value between 5 and 1990 (for SEQ ID NO: 1) or 1860 (for SEQ ID NO: 2) (one nucleotide less than the total number of nucleotides found in the full-length sequence lacking the 45 nucleotides encoding the ubiquitin monomer (SEQ ID NO: 1 or 2, respectively))." Other embodiments, a polynucleotide fragment may be referred to as "a contiguous span of at least X nucleotides, wherein X is any integer value between 5 and 2037 (for SEQ ID NO: 1) or 1906 (for SEQ ID NO: 2) (one nucleotide less than the total number of nucleotides found in the full-length sequence including the 45 nucleotides encoding the ubiquitin monomer (see FIG. 3))."

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of SEQ ID NO: 1 or SEQ ID NO: 2. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}$P, $^{35}$S, $^{3}$H, $^{125}$I) or with a molecule such as biotin, acetylaminofluorene, digoxigenin, 5-bromo-deoxyuridine, or fluorescein to provide probes that can be used in numerous applications.

The promoter sequences disclosed herein are useful for expressing operably linked nucleotide sequences. As disclosed herein, SEQ ID NO: 1 and SEQ ID NO: 2 are promoters capable of driving expression (causing the expression) of an operably linked polynucleotide sequence. As used an "isolated" or "purified" nucleic acid molecule, or biologically active fragment thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various aspect of the invention, the promoters of SEQ ID NOs: 1 or 2 can contain nucleotides encoding 1, 2, 3, 4, 5, 6, 7, 8, 9, 10, 11, 12, 13, 14 or 15 amino acids of a ubiquitin monomer. In various other aspects of the invention, the promoters of SEQ ID NOs: 1 or 2 can contain nucleotides encoding from one (1) to 76 amino acids of a ubiquitin monomer operably linked to a heterologous nucleic acids.

The nucleic acids of SEQ ID NO: 1 and SEQ ID NO: 2 are promoters. The term "promoter" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Promoter elements that enable expression, can be identified, isolated, and used with core promoters to confer expression. In this aspect of the invention, a "core promoter" is intended to mean a promoter without promoter elements generally found upstream and/or downstream of the core promoter (the minimal portion of the promoter required to properly initiate transcription which includes a Transcription Start Site (TSS) a binding site for RNA polymerase and general transcription factor binding sites. In certain embodiments, the promoters of SEQ ID NO: 1 and 2 can contain from 3 to 45 nucleotides of the ubiquitin coding region (as illustrated in FIG. 3).

The term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of this disclosure, a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events.

The promoter sequences disclosed herein, when assembled within a DNA construct such that the promoter is operably linked to a nucleotide sequence of interest, enable expression of the nucleotide sequence in the cells of a plant stably transformed with this DNA construct. The term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remain in the proper reading frame. In this manner, the nucleotide sequences for the promoters are provided in DNA constructs along with the nucleotide sequence of interest, typically a heterologous nucleotide sequence, for expression in the plant of interest.

The term "heterologous nucleotide sequence" is intended to mean a sequence that is not naturally operably linked with the promoter sequence. While this nucleotide sequence is heterologous to the promoter sequence, it may be homologous, or native; or heterologous, or foreign, to the plant host.

Fragments and variants of the disclosed promoter sequences are also encompassed. A "fragment" is intended to mean a portion of the promoter sequence. Fragments of a promoter sequence may retain biological activity (the ability to drive expression of an operably linked nucleotide sequence). Thus, for example, less than the entire promoter sequence disclosed herein may be utilized to drive expression of an operably linked nucleotide sequence of interest, such as a nucleotide sequence encoding a heterologous protein.

Accordingly, a fragment of the promoter of SEQ ID NO: 1 or SEQ ID NO: 2 can contain a biologically active portion of the promoter or it may be a fragment that can be used as a hybridization probe or PCR primer using methods disclosed below. A biologically active portion of the promoter of SEQ ID NO: 1 or SEQ ID NO: 2 can be prepared by isolating fragments of SEQ ID NO: 1 or SEQ ID NO: 2 and assessing the activity of that fragment in causing the expression of an operably linked nucleic acid sequence (such as a reporter gene). Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2025 or up to one nucleotide fewer than the total number of nucleotides in SEQ ID NO: 1 or SEQ ID NO: 2 (including or lacking the first 45 nucleotides of the ubiquitin monomer as identified in FIG. 3 (i.e., 1990 (for SEQ ID NO: 1) or 1860 (for SEQ ID NO: 2), one nucleotide less than the total number of nucleotides found in the full-length sequence lacking the 45 nucleotides encoding the ubiquitin monomer or 2037 (for SEQ ID NO: 1) or 1906 (for SEQ ID NO: 2) (one nucleotide less than the total number of nucleotides found in the full-length sequence including the 45 nucleotides encoding the ubiquitin monomer). Such fragments will usually comprise the TATA recognition sequence of the particular promoter sequence and can be obtained by use of restriction enzymes to cleave the naturally occurring promoter nucleotide sequence disclosed herein; by synthesizing a nucleotide sequence from the naturally occurring sequence of the promoter DNA sequence; or through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis and a procedure such as DNA "shuffling", are also encompassed by the instant disclosure.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence will have at least 40%, 50%, 60%, 65%, 70%, generally at least 75%, 80%, 85%, 90%, 91%, 92%, 93%, 94%, to 95%, 96%, 97%, 98%, 99% or more sequence identity to that particular nucleotide sequence (e.g., SEQ ID NO: 1) as determined by sequence alignment programs described elsewhere herein using default parameters. Biologically active variants are also encompassed. Biologically active variants include, for example, the native promoter sequence having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference. Methods for mutagenesis and nucleotide sequence alterations are well known in the art. See, for example, Kunkel (1985) *Proc. Natl. Acad. Sci, USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad Sci. USA* 94:4504-4509; Crameri et al. (1998) *Nature* 391:288-291; and U.S. Pat. Nos. 5,605,793 and 5,837,458.

The promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the invention comprise, for example, plant cells, protoplasts, tissues, callus, embryos as well as flowers, stems, fruits, ovules, leaves, or roots originating in transgenic plants or their progeny previously transformed with a DNA molecule of the invention, and therefore consisting at least in part of transgenic cells. As used herein, the term "plant cell" includes, without limitation, seeds, suspension cultures, embryos, meristematic regions, callus tissue, leaves, roots, crown, buds, apex, stems, shoots, gametophytes, sporophytes, pollen, and microspores. Monocotyledonous plants, dicotyledonous plants and ferns can be transformed with a promoter or DNA construct as disclosed herein.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. General categories of genes of interest include, for example, those genes involved in information, such as zinc fingers, those involved in communication, such as kinases, and those involved in housekeeping, such as heat shock proteins. More specific categories of transgenes, for example, include: genes that provide for decreased lignin content, increased sucrose/cellulose content, increased biomass yield, etc.; genes encoding proteins conferring resistance to abiotic stress, such as drought, flooding, temperature (heat or cold), salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a specific plant tissue, altering a plant's pathogen or insect defense mechanism, increasing the plant's tolerance to herbicides, altering tissue development to respond to environmental stress, altering biomass and cellose content and/or lignin content in a plant and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant.

It is recognized that any gene of interest can be operably linked to the promoter sequences disclosed herein and expressed in plant tissues. Thus, a DNA construct comprising a gene of interest, such as those described below, to create plants having a desired phenotype (e.g., disease, herbicide or insect resistance), to create heat or cold tolerance in a plant or to create or enhance resistance to drought or flood conditions in a plant. Accordingly, this disclosure encompasses methods that are directed to protecting plants against flooding, drought, heat, cold, fungal pathogens, bacteria, viruses, nematodes, insects, and the like. By "disease resistance" or "insect resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products. Pathogens include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Nematodes include parasitic nematodes such as root knot, cyst, and lesion nematodes, etc.

Genes encoding disease resistance traits include detoxification genes, such as against fumonisin (U.S. Pat. No. 5,792,931) avirulence (avr) and disease resistance (R) genes (Jones et al. (1994) *Science* 266:789; Martin et al. (1993) *Science* 262:1432; Mindrinos et al. (1994) *Cell* 78:1089); and the like. Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or Basta® (glufosinate) (e.g., the bar gene), or other such genes known in the art. The bar gene encodes resistance to the herbicide Basta®, the nptII gene encodes resistance to the antibiotics kanamycin and geneticin, and the ALS gene encodes resistance to the herbicide chlorsulfuron. Glyphosate resistance is imparted by mutant 5-enolpyruvl-3-phosphikimate synthase (EPSP) and aroA genes. See, for example, U.S. Pat. No. 4,940,835, which discloses the nucleotide sequence of a form of EPSPS which can confer glyphosate resistance. U.S. Pat. No. 5,627,061 also describes genes encoding EPSPS enzymes. See also U.S. Pat. Nos. 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-ketothiolase, PHBase (polyhydroxybutyrate synthase), and acetoacetyl-CoA reductase (see Schubert et al. (1988) *J. Bacteria* 170:5837-5847) facilitate expression of polyhydroxyalkanoates (PHAs).

Agronomically important traits that affect quality of grain, such as levels and types of oils, saturated and unsaturated, quality and quantity of essential amino acids, levels of cellulose, starch, and protein content can be genetically altered. Modifications include increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference. Another example is lysine and/or sulfur rich seed protein encoded by the soybean 2S albumin described in U.S. Pat. No. 5,850,016, and the chymotrypsin inhibitor from barley, Williamson et al. (1987) *Eur. J. Biochem.* 165:99-106, the disclosures of which are herein incorporated by reference.

Exogenous products include plant enzymes and products as well as those from other sources including prokaryotes and other eukaryotes. Such products include enzymes, cofactors, hormones, and the like. Examples of other applicable genes and their associated phenotype include genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

In one embodiment, DNA constructs will comprise a transcriptional initiation region comprising a promoter sequence, as disclosed herein, or variants or fragments thereof, operably linked to a heterologous nucleotide sequence whose expression is to be controlled by the promoter. Such a DNA construct is provided with a plurality of restriction sites for insertion of the nucleotide sequence to be under the transcriptional regulation of the regulatory regions. The DNA construct may additionally contain selectable marker genes.

Where appropriate, the heterologous nucleotide sequence whose expression is to be under the control of the promoter sequence disclosed herein may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Reporter genes or selectable marker genes may be included in the DNA constructs. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330. Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al.

(1990) *Plant Mol. Biol.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518). Other genes that could serve utility in the recovery of transgenic events but might not be required in the final product would include, but are not limited to, examples such as GUS (b-glucuronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19): 8115 and Luehrsen et al. (1992) *Methods Enzymol.* 216:397-414), and the maize genes encoding for anthocyanin production (Ludwig et al. (1990) *Science* 247:449).

The nucleic acid molecules disclosed herein are useful in methods of expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell.

Plant species suitable for transformation include, but are not limited to, corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza sativa*), rye (*Sectile cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Other plants suitable for transformation with a promoter as disclosed herein include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Additionally, ferns and monocots, such as maize, rice, barley, oats, wheat, sorghum, rye, sugarcane, ferns, mosses, grasses, switchgrass, pineapple, yams, onion, banana, coconut, *Miscanthus* (grass), *Brachypodium distachyon* (grass), cowpea, poplar, *Physcomitrella patens* (moss), *Pteris vittata* (fern), *Arabidopsis thaliana*, and dates can be transformed with a promoter as disclosed herein.

As used herein, "vector" refers to a DNA molecule such as a plasmid, cosmid, or bacterial phage for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

Various methods disclosed herein include introducing a nucleotide (DNA) construct into a plant. The term "introducing" is used herein to mean presenting to the plant the nucleotide construct in such a manner that the construct gains access to the interior of a cell of the plant. These methods do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant. The nucleotide constructs disclosed herein may be introduced into plants by contacting plants with a virus or viral nucleic acids. Generally, such methods involve incorporating a nucleotide construct within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889, 190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,981, 840 and 5,563,055), direct gene transfer (Paszkowski et al. (1984) *EMBO J.* 3:2717-2722), and ballistic particle acceleration (see, for example, U.S. Pat. Nos. 4,945,050; 5,879, 918; 5,886,244; 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants according to methods known in the art. See, for example, McCormick et al. (1986) *Plant Cell Reports* 5:81-84. These plants may then be grown, and either pollinated with the same transformed plant variety or different varieties, and the resulting hybrid having a desired phenotypic characteristic. Two or more generations may be grown to ensure that the expression of the desired phenotypic characteristic is stably maintained and inherited and then seeds harvested to ensure that expression of the desired phenotypic characteristic has been achieved. Thus as used herein, "transformed seeds" refers to seeds that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants are generally self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants.

All publications and patent applications are herein incorporated by reference to the same extent as if each individual publication or patent application was specifically and individually indicated to be incorporated by reference.

EXAMPLES

Example 1

An active promoter region upstream of ubiquitin coding region from a genomic library of switchgrass (*Panicum virgatum* was identified). This region at the 5' end of the ubiquitin gene contains a promoter and a putative intron, and regulates strong constitutive expression in a number of switchgrass tissue types, and is capable of driving transgene expression in switchgrass (*Panicum virgatum*), tobacco (*Nicotiana tabacum*) and a fern species (*Pteris vittata*), indicating very broad taxonomic utility in biotechnology. In addition, in-frame fusions of the first 3 and 9 amino acids of the ubiquitin gene to the 3' end of the promoter and intron also regulated high levels of transient expression of GUS in these plant species. Based on these data, PvUbi1 will be a valuable promoter candidate for monocot, dicot and fern transformation systems.

Figure 1:
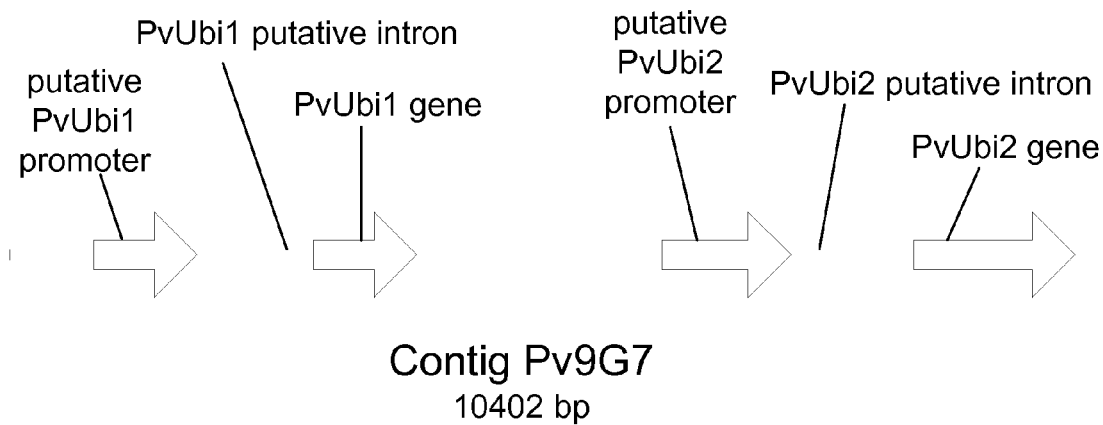
FIG. 1. Pv_9_G7 contig containing PvUbi1 and PvUbi2.
Figure 2:
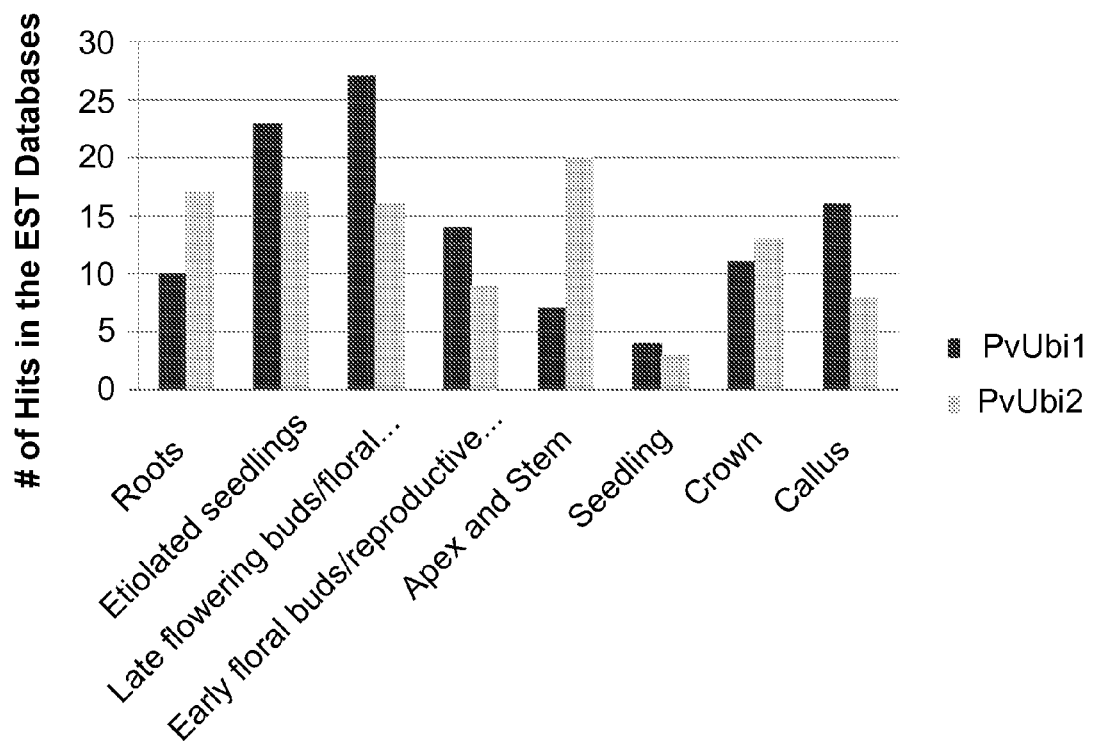
FIG. 2. Expression of PvUbi1 and PvUbi2 in a range of tissue types according to EST databases.

The promoter of interest was isolated from a fosmid and is referred to as contig Pv_9_G7 (FIG. 1). This ubiquitin gene (termed PvUbi1) was one of two ubiquitin coding regions found on this fosmid (the second gene termed PvUbi2). Both PvUbi1 and PvUbi2 showed expression in a wide range of tissue types according to the number of hits in switchgrass EST databases (FIG. 2). The translation of the sequence of these ubiquitin genes revealed four and six tandem 76 amino acid monomer repeats for PvUbi1 and PvUbi2, respectively. Additionally, putative 5' UTR introns were identified for both ubiquitin genes based on the consensus sequences CAAG/gtac at the 5' splice site and cag/ATG at the 3' splice site (FIG. 3), which are conserved throughout all characterized plant polyubiquitin genes (Binet et al. 1991; Christensen et al. 1992; Garbarino and Belknap 1994; Genschik et al. 1994; Kawalleck et al. 1993; Norris et al. 1993; Sivamani and Qu 2006; Wang et al. 2000; Wei et al. 2003). Since intron-mediated enhancement of gene expression has been confirmed in a number of plant species (Mascarenhas et al. 1990), intron regions (1291 bp for PvUbi1 and 1072 bp for PvUbi2) were included with the promoter for transgene expression. To isolate the promoter of PvUbi1, primers were designed to amplify a 1991 bp region directly upstream of the first amino acid of the PvUbi1 coding sequence. Recent studies have also suggested that in-frame fusions of the first several amino acids (3 and 9 aa) of the ubiquitin monomer downstream of the promoter/intron region can enhance gene expression and protein accumulation (Hondred et al. 1999; Sivamani and Qu 2006). Therefore, additional primers were designed to add the 9 and 27 nucleotides encoding these amino acids to the end of the promoter region (Table 1).

Figure 4C:
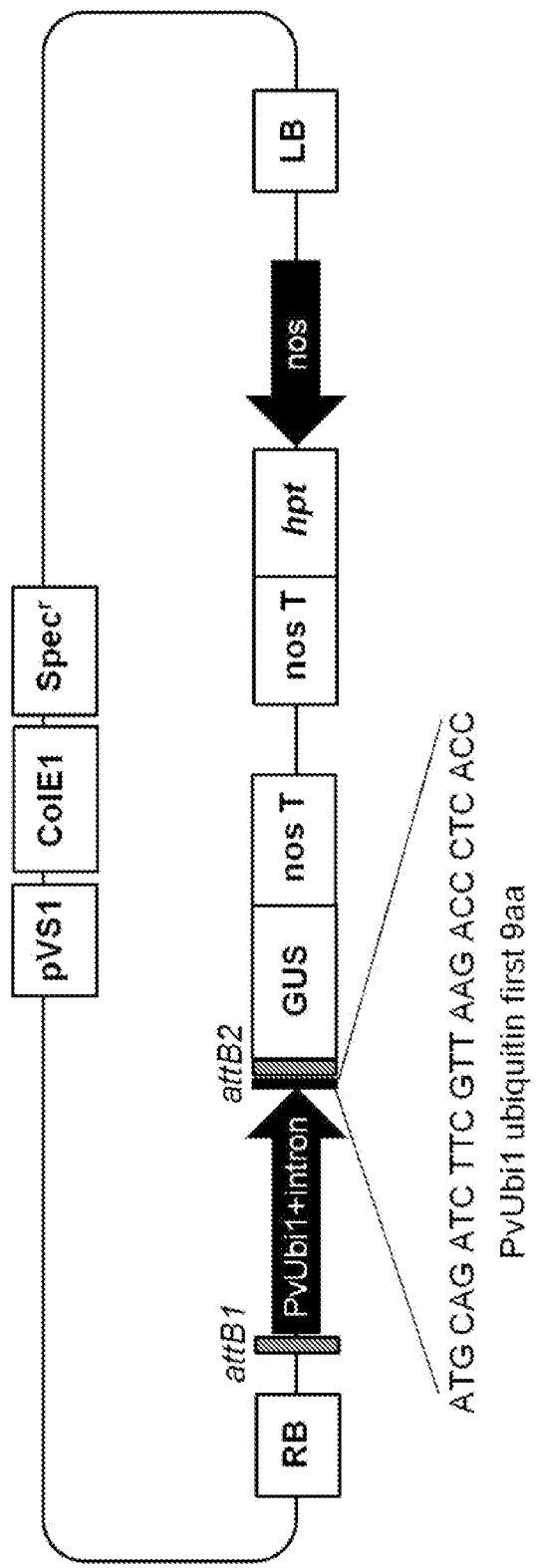
Figure 5:
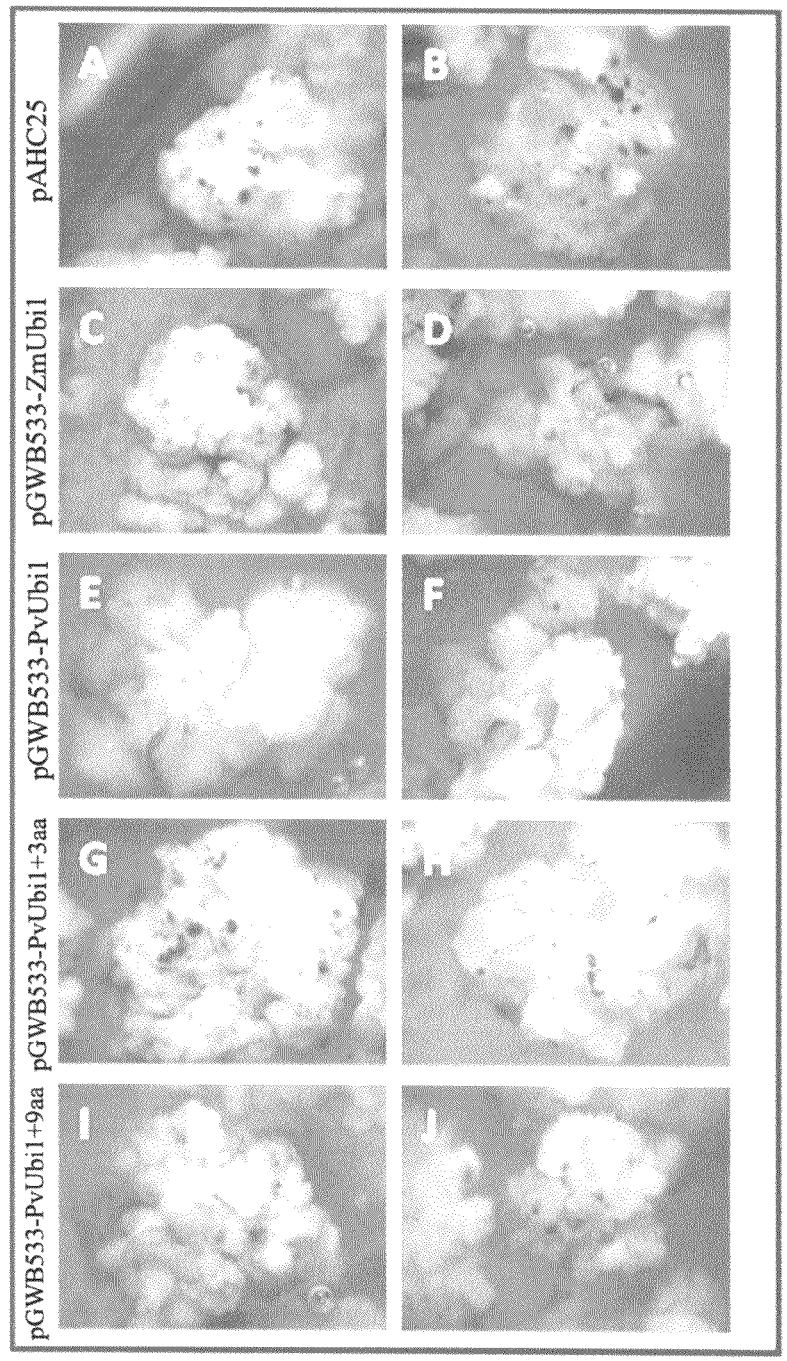
FIGS. 5A-5J. Histochemical assays of transient GUS expression in callus of switchgrass callus (Alamo II). The two pieces of calli showing the highest level of GUS expression were photographed. GUS expression was driven by the following promoters: ZmUbi1 in two different constructs, pAHC25 (a,b) and pGWB533-ZmUbi1 (c,d); PvUbi1 (e,f); PvUbi1+3aa (g,h); and PvUbi1+9aa (i,j).
Figure 6:
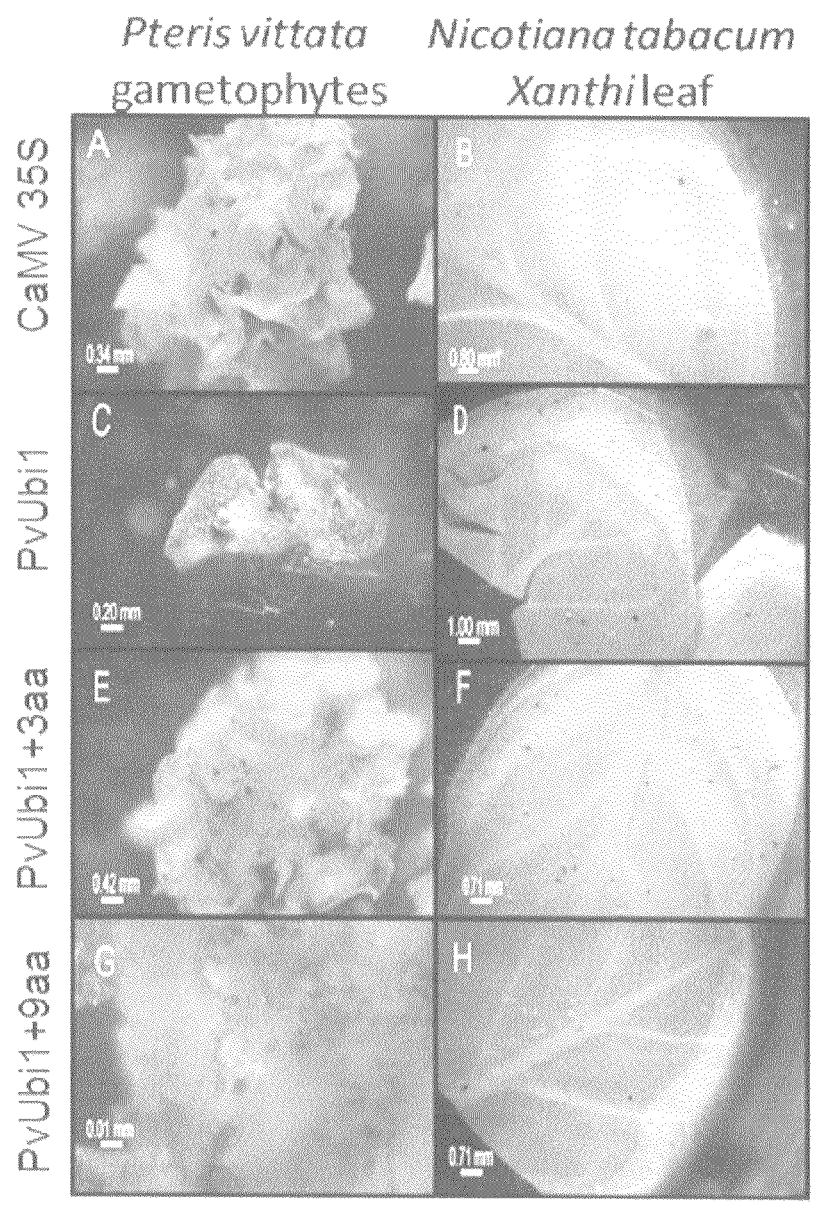
FIGS. 6A-6H. Histochemical assays of GUS expression in gametophytes of *Pteris vittata* (a,c,e,g) and *Nicotiana tabacum* Xanthi leaves (b,d,f,h). Each row constitutes GUS expression under a different promoter (1st row: pSKGUS containing CaMV 35S; 2nd row: pGWB533-PvUbi1; 3rd row: pGWB533-PvUbi1+3aa; 4th row: pGWB533-PvUbi1+9aa).

Promoter regions were amplified (termed PvUbi1, PvUbi1+3aa, and PvUbi1+9aa) and cloned into pCR8/GW/TOPO, a Gateway-compatible entry vector. Using Gateway cloning, promoters were recombined into pGWB533 backbone (Nakagawa et al. 2007), containing the GUS gene for reporter expression (FIG. 4). For promoter analysis, DNA vector constructs were transformed into switchgrass callus tissue using biolistic bombardment and transient expression was observed at 48 hrs via histochemical staining (FIG. 5). All constructs showed expression of GUS, verifying that all promoter variations can successfully be used to drive transgene expression. Two positive controls were used; pAHC25 from Christensen et al. containing the ZmUbi1 promoter (Christensen and Quail 1996), and pGWB533-ZmUbi1 containing the same ZmUbi1 promoter but placed in the identical construct as the PvUbi1 promoter variants (pGWB533) in order to eliminate any discrepancies observed due to vector backbone or size. Interestingly, expression levels of PvUbi1+3aa appear to be at least equal to those of ZmUbi1, although these expression levels were not quantified. Subsequently, constructs pGWB533-PvUbi1, pGWB533-PvUbi1+3aa and pGWB533-PvUbi1+9aa were transformed into *Nicotiana Tabacum* leaves and *Pteris vittata* gametophytes and tested for transient expression via histochemical staining (FIG. 6). Positive GUS expression was confirmed in these species as well, displaying the potential broad versatility of this promoter in monocots, dicots and ferns.

TABLE 1

Primers used for amplification of PvUbi1 promoter regions.

| Name | Sequence | Region of Amplification | Amplicon Size (bp) |
|---|---|---|---|
| PvUbi1-F1 | 5'-CCACTGGAGAGGGGCACA CACG-3' (SEQ ID NO: 4) | Promoter, intron | 1991 |
| PvUbi1-R1 | 5'-CTGCAGAAGATTAGCCAG GCAACAGG-3' (SEQ ID NO: 5) | | |
| PvUbi1-F1 | 5'-CCACTGGAGAGGGGCACA CACG-3' (SEQ ID NO: 6) | Promoter, intron and 3 aa fusion | 2000 |
| PvUbi1 +3-R1 | 5'-GATCTGCATCTGCAGAAG ATTAGCCAGG-3' (SEQ ID NO: 7) | | |
| PvUbi1-F2 | 5'-CCACTGGAGAGGGCACA CACGTCAGTGTTTGG-3' (SEQ ID NO: 8) | Promoter, intron and 9 aa fusion | 2018 |
| PvUbi1 +9-R1 | 5'-GGTGAGGGTCTTAACGAA GATCTGCATCTGCAG-3' (SEQ ID NO: 9) | | |

Example 2

Methods

Screening of a Switchgrass Fosmid Library

Using *Panicum virgatum* (cv. Alamo) leaf tissue, a fosmid library was constructed. Primers were designed to amplify fragments of 700-760 bp in size. Sequence specific primers (5'-TBACYGGMAAGACBATHACY-3', SEQ ID NO: 40, 5'-TCCTTYTGRATGTTRTARTC-3', SEQ ID NO: 41) were used to screen the library.

Fosmids identified to contain ubiquitin genes were grown in 50 ml cultures containing 50 ul of induction solution (Epicentre Biotechnologies) to increase copy number, as per manufacturer's protocol. Nuclear-free fosmid DNA was extracted using Qiagen's Large Construct Kit. Approximately 10 ug of fosmid DNA [66 ng/ul] was sheared to 2-10 kb using the Standard Hydroshear Shearing Assembly (Genomic Solutions) for 20 cycles at a speed code of 16. Sheared fragments between 3-8 kb were excised and shotgun libraries were built as described (Dubkovsky et al., 2001).

Ten clones were randomly picked from the sub-clone library and digested with EcoRI to determine the average insert size as quality control. A total of 384 sub-clones were sequenced from both directions using ABI PRISM BigDye Chemistry (Applied Biosystems, Foster, Calif.) and run on an ABI 3730. The sequences were assembled with the Phred/Phrap package and annotated in Apollo. The cumulative data represent an approximate 13-fold coverage of each fosmid. Fosmid Pv9G7B5 contained two ubiquitin genes in tandem and in the same orientation, both of which showed ≥99.5% sequence identity to switchgrass ESTs from callus, early floral development, late floral development, root, and stem tissues. Contig Pv9G7B5 was used for further isolation of switchgrass ubiquitin promoters.

Sequence Analysis

Predictions were made for the location of the ubiquitin promoters and genes within the Pv9G7B5 fosmid using FGENESH (Salamov and Solovyev, 2000) and GENSCAN (Burge and Karlin, 1997) and further confirmed using blastn in GenBank and aligning with homologous ubiquitin sequences from other plant species in AlignX (Invitrogen, Carlsbad, Calif.). Based on these results, primers were designed to amplify ~2 kb region upstream of the predicted transcription start site (Table 2). Identification of putative regulatory cis-elements within the promoter regions of PvUbi1 and PvUbi2 was performed using the PlantCARE database (web site: bioinformatics.psb.ugent.be/webtools/plantcare/html) (Lescot et al., 2002).

TABLE 2

Primers used in this study.

| Amplified Region | Primer Name | Primer Sequence | Template | Experiment |
|---|---|---|---|---|
| PvUbi1 gene | PvUbi1-3'R | 5'CAGCTTGGATGACCAATGGC-3' (SEQ ID NO: 10) | Switchgrass cDNA | 5' RACE-PCR |
| PvUbi1 gene | PvUbi1-3'F3 | 5'ATTTAGTGCTCCGCCTCC-3' (SEQ ID NO: 11) | Switchgrass cDNA | 3'RACE-PCR |
| PvUbi2 gene | PvUbi2-R2 | 5'GTGAGGGTCTTCACAAAGATCTGC-3' (SEQ ID NO: 12) | Switchgrass cDNA | 5' RACE-PCR |
| PvUbi2 gene | PvUbi2-5'F | 5'CTCACATCGTCTCATCGTTCGG-3' (SEQ ID NO: 13) | Switchgrass cDNA | 3' RACE-PCR |

TABLE 2-continued

Primers used in this study.

| Amplified Region | Primer Name | Primer Sequence | Template | Experiment |
|---|---|---|---|---|
| PvUbi1 gene | PvUbi1-RT-F4 | 5'TTGGTGCTCCGCCTGAGA-3' (SEQ ID NO: 14) | Switchgrass cDNA | qRT-PCR |
|  | PvUbi1-RT-R4 | 5' CCTGGATCTTGGCCTTCACA-3' (SEQ ID NO: 15) |  |  |
| PvUbi2 gene | PvUbi2-RT-F2 | 5' AAGTATATGCGTCATTTGGCG-3' (SEQ ID NO: 16) | Switchgrass cDNA | qRT-PCR |
|  | PvUbi2-RT-R2 | 5' ATACTGCTGCACCACCACA-3' (SEQ ID NO: 17) |  |  |
| PvAct gene | PvAct-RT-F1 | 5' CAAGATTTGGAGATCCCGTG-3' (SEQ ID NO: 18) | Switchgrass cDNA | qRT-PCR |
|  | PvAct-RT-R1 | 5' AATGCTCCACGGCGAACAG-3' (SEQ ID NO: 19) |  |  |
| CaMV 35S promoter | 35S-F | 5'-AGATTAGCCTTTTCAATTTCAG-3' (SEQ ID NO: 20) | pBIN-m-GFP5-er | Promoter Validation |
|  | 35SR | 5'-CGTGTTCTCTCCAAATGAAA-3' (SEQ ID NO: 21) |  |  |
| 2x35S promoter | d35S-F | 5'-GGTCAACATGGTGGAGCACGAC-3' (SEQ ID NO: 22) | pMDC32 | Promoter Validation |
|  | d35S-R | 5'-GGGATCCTCTAGAGTCGAGGTCC-3' (SEQ ID NO: 23) |  |  |
| OsAct1 promoter | OsAct1-F | 5'-CTCGAGGTCATTCATATGCT-3' (SEQ ID NO: 24) | pCOR113 | Promoter Validation |
|  | OsAct1-R | 5'-TCTACCTACAAAAAAGCTCC-3' (SEQ ID NO: 25) |  |  |
| ZmUbi1 promoter | ZmUbi1-F | 5'-TGCAGTGCAGCGTGACCCGG-3' (SEQ ID NO: 26) | pAHC25 | Promoter Validation |
|  | ZmUbi1-R | 5'-TGCAGAAGTAACACCAAACAACAGGG-3' (SEQ ID NO: 27) |  |  |
| PvUbi1 promoter | PvUbi1-F | 5'-CCACTGGAGAGGGGCACACACG-3' (SEQ ID NO: 28) | Pv9G7 contig | Promoter Validation |
|  | PvUbi1-R | 5'-CTGCAGAAGATTAGCCAGGCAACAGG-3' (SEQ ID NO: 29) |  |  |
| PvUbi1 +3 promoter | PvUbi1-F | 5'-CCACTGGAGAGGGGCACACACG-3' (SEQ ID NO: 30) | Pv9G7 contig | Promoter Validation |
|  | PvUbi1 +3-R | 5'-GATCTGCATCTGCAGAAGATTAGCCAGG-3' (SEQ ID NO: 31) |  |  |
| PvUbi1 +9 promoter | PvUbi1 +9-F | 5'-CCACTGGAGAGGGGCACACACGTCAGTG-3' (SEQ ID NO: 32) | Pv9G7 contig | Promoter Validation |
|  | PvUbi1 +9-R | 5'-GGTGAGGGTCTTAACGAAGATCTGCATCTGCAG-3' (SEQ ID NO: 33) |  |  |
| PvUbi2 promoter | PvUbi2-F | 5'-GAAGCCAACTAAACAAGACCATAACCATGGTG-3' (SEQ ID NO: 34) | Pv9G7 contig | Promoter Validation |
|  | PvUbi2-R | 5'-CTGCAAAAGAGAACCAGACAACAGGG-3' (SEQ ID NO: 35) |  |  |
| PvUbi2 +3 promoter | PvUbi2-F | 5'-GAAGCCAACTAAACAAGACCATAACCATGGTG-3' (SEQ ID NO: 36) | Pv9G7 contig | Promoter Validation |
|  | PvUbi2 +3-R | 5'-GATCTGCATCTGCAAAAGAGAACCAGAC-3' (SEQ ID NO: 37) |  |  |
| PvUbi2 +9 promoter | PvUbi2-F | 5'-GAAGCCAACTAAACAAGACCATAACCATGGTG-3' (SEQ ID NO: 38) | Pv9G7 contig | Promoter Validation |
|  | PvUbi2 +9-R | 5'-GGTGAGGGTCTTCACAAAGATCTGCATC-3' (SEQ ID NO: 39) |  |  |

RACE-PCR

The full-length cDNA (including 5'UTRs, coding sequence and 3'UTRs) of the PvUbi1 and PvUbi2 genes were identified using the 5'RACE-PCR and 3'RACE-PCR, respectively, in the GeneRacer™ kit (Invitrogen, Carlsbad, Calif., USA). Total RNA extractions from leaves of switchgrass cv. Alamo were performed using the TRI reagent (MRC, Cincinnati, Ohio). Approximately 3 μg of total RNA were used for reverse transcription to generate cDNA. To remove trace contamination of genomic DNA, RNA was treated with DNase I according to manufacturer's instructions (Promega, Madison, Wis., USA). The resulting 5' and 3'UTRs of cDNA of both genes were amplified with the GeneRacer™ kit and cloned into pCR® 8/GW/TOPO® vector (Invitrogen) for sequence confirmation and analysis. The primers used to are listed in Table 2.

Quantitative Real-Time PCR (qRT-PCR)

Levels of Pvubi-1 and Pvubi-2 mRNA abundance were measured using quantitative reverse transcriptase PCR (qRT-PCR) in a variety of switchgrass tissues. Flower, leaf, stem and root tissues of 3-month-old greenhouse-grown switchgrass (cv. Alamo), and callus generated from inflorescences of genotype Alamo 2 were used for RNA extraction. Total RNA was isolated from the respective tissues using Tri-Reagent (Molecular Research Center, Cincinnati, Ohio), and DNA contamination was removed with DNase treatment (Promega, Madison, Wis.) following the manufacturer's instructions. Switchgrass actin gene (PvAct) was used as an internal control. Specific primers to the corresponding genes were designed (Table 2). These primers amplified a single product for each corresponding gene, as confirmed by the melting temperature of the amplicons and gel electrophoresis. Approximately 3 μg of the total RNA from three independent biological experiments was synthesized into first strand cDNA using High Capacity cDNA Reverse Transcription kit (Applied Biosystems, Foster City, Calif.). qRT-PCR was conducted in triplicate using Power SYBR Green PCR master mix (Applied Biosystems) according to the manufacturer's protocol. Relative quantification was performed using the standard curve method, and transcript accumulation of each gene was normalized to the quantity of expressed switchgrass actin gene. For quality assurance purposes, only qRT-PCR assays that resulted in standard curves with the following parameters were considered: i) linear standard curve throughout the measured area, ii) standard curve slope between −3.5 and −3.2, and iii) R2 value above 0.99.

Expression Vector Construction

All promoters (ZmUbi1, OsAct1, CaMV 35S, d35S, PvUbi1, PvUbi1+3, PvUbi1+9, PvUbi2, PvUbi2+3, PvUbi2+9) were amplified with specific primer sets shown in Table 2 and cloned into pCR8/GW/TOPO (Invitrogen, Carlsbad, Calif.). The PvUbi1 and PvUbi2 promoter variants were derived from the Pv9G7B5 contig mentioned above, the ZmUbi1 promoter from pAHC25 (Christensen and Quail, 1996), the OsAct1 promoter from pCOR113 (McElroy et al., 1991), the CaMV 35S promoter from pBin-m-gfp5-ER (Haseloff et al., 1997), and the d35S promoter from pMDC32 (Curtis and Grossniklaus, 2003). DNA was confirmed by restriction enzyme digests for orientation, and clones containing the proper orientation were sequence verified at the University of Tennessee Molecular Biology Resource Facility (UT-MBRF). These amplified promoter regions were introduced from the pCR8/GW/TOPO backbone into the binary vectors pGWB533 and pGWB535 (Nakagawa et al., 2007) using the Gateway® LR Clonase® II enzyme mix (Invitrogen, Carlsbad, Calif.). The pGWB533 vector contains the Gateway® cassette upstream of the gus coding region (GUS), resulting in a promoter-GUS fusion construct. Likewise, the pGWB535 vector contains the Gateway® cassette upstream of the luciferase coding region (LUC), resulting in a promoter-LUC fusion construct.

DNA Particle Bombardment of Switchgrass and Rice Callus

Transient biolistic transformation of rice (Oryza sativa L. japonica) cv. Taipei 309 and switchgrass (Panicum virgatum L.) cv. Alamo, genotype ST1 embryogenic callus cultures was accomplished using the PSD-1000. The co-bombardment used the vectors pGWB533 containing promoter variants fused to the uidA gene encoding for β-glucuronidase (GUS), including 2x35S; and pGWB535-ZmUbi1:Luciferase. Microprojectile preparation essentially followed Trick et al. (1997) with the DNA amount increased from 8.33 to 300 ng per bombardment total (1:1 vector ratio), and 10 mg of 0.6 μm diameter Au used instead of 12 mg of 1 μm particles (all reagents from bio-rad.com). Callus cultures of Taipei 309 were induced and maintained as previously described on modified NB medium (Chen et al., 1998). Switchgrass inflorescences were induced as previously described with two exceptions, sucrose substituted maltose, and the pH was raised from 5.5 to 5.8 (Alexandrova et al., 1996). Callus of ST1 was enduced from immature inflorescences on solid N6E medium and maintained for 4-months with subcultures at 3-week intervals (web site agron.iastate.edu/ptf/protocol/Embryo%20bb.pdf). Four-days prior to bombardment, callus tissue of Taipei 309 and ST1 was subcultured onto NB and N6E callus maintenance medium, respectively. Twenty calli were arranged in the center of a 2.5-cm target, whereas each piece of tissue was 2-mm in diameter. The PSD-1000 was fired at 7,584 kPa (1,100 PSI), after a 4 hour osmotic adjustment period on NBO (Chen et al., 1998) or N6-Osmoticum (www.agroniastate.edu/ptf/protocol/Embryo%20bb.pdf), for rice and switchgrass, respectively. Twenty-four hours post-bombardment, all callus tissue per plate was removed and ground in 500 μl of ONE-Glo™ Luciferase Assay buffer (promega.com) to perform protein extractions. The cell lysates were centrifuged at 13,000 g for 15 minutes. The soluble protein extracts produced were used for 4-Methylumbeiliferyl Beta-D-Glucuronide (MUG) and luciferase assays (Leckie et al., 1994; Sivamani et al., 2009). For biolistic bombardment of Pteris vittata, the same protocol as above was performed, increasing the DNA amount to 2 μg per bombardment. Pteris vittata spores were surface sterilized with 10% (v/v) bleach and 70% (v/v) ethanol and plated on solid 0.5 Murashige and Skoog (MS) medium with 20 g L$^{-1}$ sucrose (0.5 MS 20 gS). After three weeks, gametophytes were subcultured onto the same medium to undergo biolistic bombardment.

MUG and LUC Assays

For quantification of GUS activity, 2 μl of protein extract was assayed with MUG (4-methylumbelliferyl-β-D-glucuronide) as substrate using the BioTek® Synergy 2 fluorometer (biotek.com) at an excitation of 360/40 nm as per Jefferson et al. (1987), and an emission of 460/40 nm and read in duplicate. All results from MUG assays were expressed as pmole MU (4-methylumbelliferone) released min$^{-1}$ mg$^{-1}$ total protein. Luciferase activity was quantified by the BioTek® Synergy 2 as outlined by the luciferase assay procedures of the ONE-Glo™ Luciferase Assay kit by Promega (promega.com) using 10 μl of protein extraction. Normalization of the MUG data was accomplished using the luciferase cassette as per Schledzewski et al. (1994).

The strength of each promoter is reported relative to dual CaMV 35S (2x35S), reported as 1, to create a dimensionless value of relative promoter strength.

Agrobacterium-Mediated Transformation of Tobacco

Appropriate vectors were transformed into Agrobacterium tumefaciens strain EHA105 as previously described (Hofgen and Willmitzer, 1988). EHA105 cells were maintained in liquid YEP medium (1.0% w/v peptone, 1.0% yeast extract, 0.5% NaCl) and all incubations were done at 28° C. For Agrobacterium-mediated transformation, Nicotiana tabacum cv. Xanthi seeds were surface sterilized in 20% ethanol and 10% dilution of sodium hypochlorite (5.25% sodium hypochlorite, Fischer Scientific) and subsequently plated on semi-solid MSO six weeks prior to transformation. MSO consists of MS basal medium (Murashige and Skoog, 1962), B5 vitamins (Gamborg et al., 1968), with 3.0% sucrose and 0.2% Gelrite® gellan gum, pH adjusted to 5.8. On the day of the genetic transformation, the appropriate EHA105 cell cultures were spun down for 5 min. at 5000 rpm and resuspended in 2.5 ml liquid DBI medium (4.3 g/L MS salt mixture, 100 mg/L myoinositol, 4 mg/L thiamine, 30 g/L sucrose, 8 g/L agar, pH adjusted to 5.6). *Nicotiana tabacum* leaf explants were cut and placed into the resuspended EHA105 cell culture in a sterile Petri dish for 30 min. Afterwards, the explants were moved to semi-solid MSO for 2 days to co-cultivate. Explants were moved to semi-solid DBI with 50 µM hygromycin and 400 µM timentin and subcultured every two weeks until shoot formation. Shoots were moved to semi-solid MSO with appropriate selection for rooting. Once rooted, plants were moved to soil to harden off. After one month in a controlled environmental chamber at 28° C. with 16-h-day/8-h-night cycle, plants were transplanted to the greenhouse. $T_1$ seeds were collected after set, labeled, and sterilized as before and plated on MSO with 50 µM hygromycin for selection.

Histochemical Staining

Plant tissues were stained in GUS solution (50 mg of 5-bromo-4-chloro-3-indolyl glucuronide (X-Gluc), 5 ml of DMSO, 10 mL of $KPO_4$ buffer, 100 µl of Triton X-100, and $H_2O$ to a final volume of 50 mL) in microwell plates and placed in a 37° C. incubator overnight. Intact seedling and leaf stains were made homogenous by vacuum infiltrating in solution for 30 minutes. For optimal visualization of stained tissues, chlorophyll were removed by repeatedly washing the tissue with 3:1 ratio of EtOH and acetic acid, ultimately storing tissue samples in 70% EtOH for microscopy and imaging.

Identification and Isolation of PvUbi1 and PvUbi2

In order to isolate DNA sequences of interest in switchgrass, a genomic DNA fosmid library was constructed. This library was screened for potential polyubiquitin gene candidates, and a 10.4 kilobase (kb) contig termed Pv9G7B5 was targeted as a result of it containing two independent polyubiquitin gene sequences, termed switchgrass (*Panicum virgatum* L.) ubiquitin 1 (PvUbi1) and 2 (PvUbi2). FIG. 7 shows a genomic map and organizational diagram of the Pv9G7B5 contig. The PvUbi1 and PvUbi2 promoters, the 5' UTR exons, introns, the polyubiquitin coding sequences, and the 3' UTR regions have all been characterized as described below and deposited in GenBank (accession numbers HM209467 and HM209468).

Sequence Analysis of PvUbi1 and PvUbi2

For PvUbi1, the sequence data revealed an open reading frame of 918 bp encoding four tandem, head-to-tail repeats of 228 bp, commonly referred to as ubiquitin monomer repeats, with minimal sequence variations from one repeat to another. Similar results were found from sequence analysis of PvUbi2, although instead of four repeats, the coding sequence contained five tandem, head-to-tail repeats resulting in a coding region of 1146 bp. The ubiquitin monomers of PvUbi1 and PvUbi2 contained identical amino acid sequences to each other, as well as to ubiquitin amino acid sequences from other plant species including maize (Christensen et al., 1992), *Arabidopsis* (Burke et al., 1988) and rice (Wang et al., 2000; Sivamani and Qu, 2006). The isolated promoter region of PvUbi1 spans 607 bp of the 5' region upstream from the transcriptional initiation site. This region, along with the 93 bp 5' UTR non-coding exon and 1291 5' UTR intron, was cloned for further analysis. For PvUbi2, the isolated promoter region was longer than PvUbi1, spanning a range of 692 bp upstream of the transcriptional initiation site. The 5' UTR exon (97 bp) and the 5' UTR intron (1072 bp) were also characterized together with the PvUbi2 promoter region. The full sequences of the PvUbi1 and PvUbi2 promoter regions are displayed in FIGS. 8A and 8B.

The PlantCARE Database (Lescot et al., 2002) was queried for putative cis-element sequences within the 5' promoter regions of PvUbi1 and PvUbi2 that may be bound by trans-acting proteins during different plant responses and developmental stages. A variety of putative motifs were identified in the 5' promoter regions of PvUib1 and PvUbi2 (underlined in FIGS. 8A and 8B). For PvUbi1, these include a cis-acting regulatory element essential for anaerobic induction (TGGTTT, positions −577 to −572), part of a conserved DNA light responsive module (ATTAATTTTACA (SEQ ID NO: 42), positions −350 to −339), a cis-acting regulatory element involved in light responsiveness (CACGTC, positions −589 to −584), three light responsive elements (CC(G/A)CCC, positions −221 to 216; −170 to −165; and −54 to −49), two cis-acting regulatory elements involved in response to methyl jasmonate (MeJA) (CGTCA, positions −392 to −388; −77 to −73), a cis-acting element involved in low-temperature responsiveness (CCGAAA, positions −112 to −107), a cis-acting regulatory element required for endosperm expression (GTCAT, positions −391 to −387), a MYB transcription factor binding site involved in drought-inducibility (TAACTG, positions −312 to −307), along with three CAAT boxes (positions −553 to −550; −538 to −535; and −458 to −455) and a TATA box (TATATAAA, positions −33 to −26). For PvUbi2, the putative motifs included a cis-acting regulatory element related to meristem expression (GCCACT), a cis-acting regulatory element related to meristem specific activation (CCGTCC), an enhancer-like element involved in anoxic specific inducibility (CCCCCG), a cis-acting element involved in low-temperature responsiveness (CCGAAA), two cis-acting regulatory elements required for endosperm expression (GTCAT), a light responsive element (CC(G/A) CCC), two CAAT boxes ( ) and a TATA box (TAAATA, positions −32 to −27).

By studying the genomic DNA region, putative introns were identified immediately upstream of the ATG start codons in the PvUbi1 and PvUbi2 genes. These intron sequences were identified based on the consensus sequences CAAG/gtac at the 5' splice site and cag/ATG at the 3' splice site (shown in FIGS. 8A and 8B), which have been identical for all reported polyubiquitin genes from plants (Binet et al., 1991; Christensen et al., 1992; Kawalleck et al., 1993; Norris et al., 1993; Garbarino and Belknap, 1994; Genschik et al., 1994; Wang et al., 2000; Wei et al., 2003; Sivamani and Qu, 2006). To verify these intron splice sites and identify the transcriptional initiation site, switchgrass cDNA was isolated, amplified using RACE-PCR with primers specific for PvUbi1 or PvUbi2, cloned and sequenced. For PvUbi1, results of the RACE-PCR revealed a transcriptional initiation site at an adenine (A) located 1384 bases upstream from the ATG translational initiation codon of the ubiquitin gene. Subsequently, the transcriptional initiation site for PvUbi2 was identified at an adenine (A) 1169 bp upstream from the translational initiation codon of the ubiquitin gene. Using cDNA clones from the RACE-PCR, along with expressed sequence tags (ESTs) from GenBank and Tobias et al. (Tobias et al., 2008), the putative intron splice sites were confirmed, revealing 1291 and 1072 bp introns present in PvUbi1 and PvUbi2, respectively. The PvUbi1 and PvUbi2 introns showed low identity when compared to each other (53%), similar to what has been reported when comparing rice ubiquitin introns (Wang et al., 2000).

Tissue Expression Profiles of PvUbi1 and PvUbi2

Examination of switchgrass ESTs from the GenBank and Tobias et al. (Tobias et al., 2008) databases revealed expression of PvUbi1 and PvUbi2 in all tissue types and stages, including leaf, root, apex and stem, crown, callus, early floral buds and reproductive tissue, late flowering buds and seed development, and etiolated seedlings. To confirm these in silico data, specific primers were designed for PvUbi1 and PvUbi2 to perform quantitative reverse transcriptase-PCR (qRT-PCR) in different switchgrass tissues (FIG. 9). Quantitative RT-PCR results confirm that both PvUbi1 and PvUbi2 are expressed in all tissues tested (leaf, flower, stem, root and callus). PvUbi2 showed higher levels of expression in all tissues except stem when compared to PvUbi1. Furthermore, PvUbi2 showed high levels of expression in root tissue, more than three-fold higher when compared to the control actin (PvAct) gene (actin expression levels were set to the value 1 in all tissue types). Additional sequence data suggests that while the 5' and 3' UTRs of PvUbi2 are unique, more than one copy of ubiquitin genes may exist in switchgrass containing identical 5' and 3' UTRs to PvUbi1 (data not shown). This data could overstate the levels of mRNA abundance shown in FIG. 9 for PvUbi1; however, these findings cannot be fully validated until the sequenced switchgrass genome is available.

Construction of Vectors Containing PvUbi1 and PvUbi2 Promoters Driving GUS Expression The capabilities of the PvUbi1 and PvUbi2 promoters for regulating transgene expression were evaluated through the construction of expression vectors as shown in FIG. 10. Since intron-mediated enhancement of gene expression has been confirmed in a number of plant species (Mascarenhas et al., 1990; Rose and Beliakoff, 2000), and more specifically, multiple ubiquitin promoters have shown enhanced transgene expression during analysis when the intron is included in the promoter region (Mascarenhas et al., 1990; Sivamani and Qu, 2006), the intron regions (1291 bp for PvUbi1 and 1072 bp for PvUbi2) were joined with their respective 5' upstream promoter regions during vector construction. Moreover, the fusion of ubiquitin to the N terminus of another protein leads to site-specific and highly efficient cleavage, resulting in free ubiquitin and free protein of interest in the cell (Varshaysky, 2005). These fusions are not only efficiently processed and cleaved by ubiquitin-specific proteases, but can also lead to enhanced gene expression and protein accumulation (Hondred et al., 1999; Sivamani and Qu, 2006). In fact, plant vectors are now available employing ubiquitin fusions for the coexpression and cleaving of two proteins from a single transcript (Walker and Vierstra, 2007). This approach has also been used for the enhancement of ubiquitin promoters in driving transgene expression by the addition of amino acids from the N terminus of the ubiquitin gene to the 5' upstream region containing the regulatory elements, non-coding exon, and intron, although differing lengths of amino acid sequences have been used (Wang et al., 2000; Sivamani and Qu, 2006). Sivamani and Qu validated that only the first three amino acids of the ubiquitin monomer are needed for the enhancing effect (Sivamani and Qu, 2006). Therefore, additional promoter variants (as shown in FIG. 10) were tested containing three and nine amino acid fusions downstream of the PvUbi1 and PvUbi2 intron sequences to test for increased transgene expression and protein accumulation.

Transient and Stable GUS Expression Regulated by the PvUbi1 and PvUbi2 Promoter Variants For promoter analysis, vector constructs were transformed into switchgrass callus tissue by particle bombardment and transient GUS expression was observed after histochemical staining (FIGS. 11A-D). All constructs showed expression of GUS, verifying that all promoter variations of PvUbi1 and PvUbi2 can successfully be used to drive transgene expression. Based on this preliminary data, positive controls of other commonly used plant promoters were constructed using the identical DNA backbone (pGWB533) as the PvUbi1 and PvUbi2 promoter variants in order to eliminate any discrepancies observed due to vector backbone or vector size.

To quantify the expression levels of GUS using the MUG assay (Jefferson, 1987), the pGWB533 constructs containing the PvUbi1 and PvUbi2 promoter variants were introduced into rice and switchgrass callus by particle bombardment along with positive controls (pGWB533-2x35S and pGWB533-ZmUbi1 for rice and switchgrass, respectively). Additionally, pGWB535-ZmUbi1 (containing the ZmUbi1 promoter and the luciferase (LUC) coding sequence) was co-bombarded as an internal control to improve the reliability and reproducibility of transient expression data as previously reported (Lepetit et al., 1991; Schledzewski and Mendel, 1994). The GUS and LUC activities were detected and the calculations of the MUG to LUC assay ratios are described in the Materials and Methods.

In switchgrass, all PvUbi1 and PvUbi2 promoter variants were compared to ZmUbi1, a common promoter that has been used extensively in monocots to drive transgene expression. Promoters PvUbi1+9, PvUbi2 and PvUbi2+9 all resulted in higher levels of GUS expression when compared to ZmUbi1, while expression levels driven by PvUbi1, PvUbi1+3 and PvUbi2+3 were lower than those of ZmUbi1. In rice, all PvUbi1 and PvUbi2 promoter variants resulted in higher levels of transient GUS expression than the 2x35S promoter (FIG. 12B). Surprisingly, when comparing rice (FIG. 12A) to switchgrass (FIG. 12B), expression levels of all the PvUbi1 and PvUbi2 promoter variants were higher in rice except for the PvUbi1+9 promoter. Most strikingly, when the PvUbi1 and PvUbi2 promoter variants were compared directly to each other in rice and switchgrass with normalization to the same promoter control (pGWB533-2x35S), PvUbi2+3 showed a 3.5- to 4-fold higher level of expression in rice over switchgrass (FIG. 12C). This reveals that one or more of these switchgrass promoters have potential for driving high levels of transgene expression in rice as well as switchgrass.

In addition, expression levels were compared between the PvUbi1 and PvUbi2 promoters and their three (PvUbi1+3 and PvUbi2+3) and nine (PvUbi1+9 and PvUbi2+9) amino acid ubiquitin fusion variants. The PvUbi1+9 construct showed equal to or higher levels of expression in rice and switchgrass when compared to the PvUbi1 and PvUbi1+3 constructs, suggesting that the nine amino acid fusion has an additive effect for transgene expression levels. However, the results for the PvUbi2 constructs were more varied, with PvUbi2 showing the highest level in switchgrass and PvUbi2+3 showing the highest level of expression in rice (FIGS. 12A and 12B). While these data demonstrate that all PvUbi1 and PvUbi2 promoter variants can regulate sufficient levels of transgene expression in rice and switchgrass, it remains a challenge to make conclusive statements on the relative expression of these promoters from transient particle bombardment assays alone. Stable transformants of rice and switchgrass, along with other monocot species, are needed to confirm the capabilities of these promoters to drive transgene expression and the range of tissue in which these promoters are constitutively expressed.

Subsequently, PvUbi1 and PvUbi2 vector construct variants were stably transformed into tobacco (Nicotiana tabacum L. cv. Xanthi) to evaluate expression levels of these promoters in a dicot model expression system. Stably transformed T0 plants were randomly selected and grown to seed for generation of T1 plants. Expression of GUS from the PvUbi1 constructs (PvUbi1, PvUbi1+3, PvUbi1+9) could not be visually observed in T1 seedlings at 10 and 17 days after germination (data not shown). However, the PvUbi2 constructs (PvUbi2, PvUbi2+3, PvUbi2+9) exhibited detectable levels of GUS staining in the vascular tissue of leaves, stems, and roots at 10 and 17 days, with PvUbi2+3 showing the highest levels of expression followed by PvUbi2+9 (FIGS. 13A-C). In addition, there was no visible induction of GUS expression from the promoter constructs in tobacco following heat shock treatment for 60 minutes at 42° C. While the heat shock inducibility of ubiquitin promoters has been used to increase GUS expression in sugarcane (Wei et al., 2003), heat shock induction has been reported to have a variety of effects on polyubiquitin promoters including up-regulation (Binet et al., 1991; Christensen et al., 1992; Wang et al., 2000; Sivamani and Qu, 2006), down-regulation (Garbarino et al., 1992) and no change (Kawalleck et al., 1993). The heat shock element consensus sequence (CNNGAANNTTCNNG, SEQ ID NO: 43) as reported by Pelham (Pelham, 1982) was not found in the promoter regions of PvUbi1 or PvUbi2 and no heat shock elements were identified from the PlantCARE database queries (Lescot et al., 2002).

Since the PvUbi2 constructs showed expression in seedlings, plants containing these constructs (and excluding the PvUbi1 constructs) were grown to maturity for further analysis and histochemical staining (FIGS. 14A-D). Fully grown T1 plants showed expression of GUS in the pollen, pistil and leaves for all PvUbi2 constructs (PvUbi2, PvUbi2+3, PvUbi2+9). Once again, PvUbi2+3 showed the highest levels of expression, followed by PvUbi2+9. As expected, expression of GUS observed by histochemical staining was higher when driven by the 2x35S promoter for seedlings and mature plants. Expression of GUS in mature leaves under the control of all PvUbi2 promoter variants was specific to the vascular tissue. GUS expression levels driven by PvUbi2+3 and PvUbi2+9 in mature T1 plants were lower than those in seedlings. These observations are consistent with the findings that ubiquitin levels are increased in younger plant tissues (Burke et al., 1988; Cornejo et al., 1993).

The fern species *Pteris vittata* has become a useful model system for environmental phytoremediation and elucidation of the pathways involved (Xie et al., 2009). However, even with the attention that *Pteris vittata* has received, it still remains notoriously difficult to genetically transform. Some of the limitations to genetic transformation include the availability and optimization of promoters for driving transgenes. Therefore, the PvUbi2 promoter variants were tested for transient expression by particle bombardment in gametophytes of *Pteris vittata* (FIGS. 15A-H). Positive GUS expression was confirmed for all PvUbi2 promoter variants by histochemical staining, demonstrating the potential broad versatility of these promoters in ferns as well as monocot and dicot species. Higher GUS expression was observed in the PvUbi2 promoter variants when compared to the PvUbi1 promoter variants. Therefore, subsequent experiments were performed on the PvUbi2 promoters. GUS expression was measured by manually counting blue foci after histochemical staining to obtain qualitative data comparing the promoters (FIG. 16). All PvUbi2 promoter variants resulted in higher foci counts when compared to 2x35S. Additionally, the number of foci increased for the PvUbi2+3 and PvUbi2+9 promoters when compared to PvUbi2, with PvUbi2+9 resulting in the highest number of foci. This suggests the additive effect of the ubiquitin amino acid fusions to the PvUbi2 promoter.

Thus, we have identified two ubiquitin genes (PvUbi1 and PvUbi2) from a genomic library of switchgrass and isolated, from the 5' upstream regions of PvUbi1 and PvUbi2, active promoter regulatory elements and introns, and are capable of driving strong constitutive expression in switchgrass (*Panicum virgatum*). Vectors containing PvUbi1 and PvUbi2 promoters and variations of these promoters (fusions of three and nine amino acids from their respective ubiquitin coding sequences) drove high levels of expression rice, and PvUbi2 promoter variants also drove high levels of expression in tobacco and *Pteris vittata* (fern species). Stable transformation of tobacco with PvUbi2+3 and PvUbi2+9 promoter variants showed expression in seedlings as well as the leaves, pistils and pollen of mature plants. Based on these data, PvUbi1 and PvUbi2 are valuable promoter candidates for monocot, dicot and fern transformation systems.

REFERENCES

Alexandrova K S, Denchev P D, Conger B V (1996) In vitro development of inflorescences from switchgrass nodal segments. Crop Science 36: 175-178.

Binet M-N, Weil J-H, Tessier L-H. 1991. Structure and expression of sunflower ubiquitin genes. Plant Molecular Biology 17(3):395-407.

Burge C, Karlin S (1997) Prediction of complete gene structures in human genomic DNA. Journal of Molecular Biology 268: 78-94.

Burke T, Callis J, Vierstra R D (1988) Characterization of a polyubiquitin gene from *Arabidopsis thaliana*. Molecular and General Genetics 213: 435-443.

Chen L, Zhang S, Beachy R N, Fauquet C M (1998) A protocol for consistent, large scale production of fertile transgenic rice plants. Plant Cell Reports 18: 25-31.

Christensen A H, Sharrock R A, Quail P H (1992) Maize polyubiquitin genes: structure, thermal perturbation of expression and transcript splicing, and promoter activity following transfer to protoplasts by electroporation. Plant Molecular Biology 18: 675-689.

Christensen A H, Quail P H. 1996. Ubiquitin promoter-based vectors for high-level expression of selectable and/or screenable marker genes in monocotyledonous plants. Transgenic Research 5:213-218.

Christensen A H, Sharrock R A, Quail P H. 1992. Maize polyubiquitin genes: structure, thermal perturbation of expression and transcript splicing, and promoter activity following transfer to protoplasts by electroporation. Plant Molecular Biology 18(4):675-689.

Cornejo M-J, Luth D, Blankenship K M, Anderson O D, Blechl A (1993) Activity of a maize ubiquitin promoter in transgenic rice. Plant Molecular Biology 23: 567-581.

Curtis M D, Grossniklaus U (2003) A Gateway Cloning Vector Set for High-Throughput Functional Analysis of Genes in Planta. Plant Physiol. 133: 462-469.

Dubcovsky, Jorge, Wusirika Ramakrishna, Phillip J. San-Miguel, Carlos S. Busso, Liuling Yan, Bryan A. Shiloff, and Jeffrey L. Bennetzen. Comparative Sequence Analysis of Colinear Barley and Rice Bacterial Artificial Chromosomes. Plant Physiol, March 2001, Vol. 125, pp. 1342-135.

Garbarino J E, Rockhold D R, Belknap W R (1992) Expression of stress-responsive ubiquitin genes in potato tubers. Plant Molecular Biology 20: 235-244.

Garbarino J E, Belknap W R. 1994. Isolation of a ubiquitin-ribosomal protein gene (ubi3) from potato and expression of its promoter in transgenic plants. Plant Molecular Biology 24(1):119-127.

Genschik P, Marbach J, Uze M, Feuerman M, Plesse B, Fleck J. 1994. Structure and promoter activity of a stress and developmentally regulated polyubiquitin-encoding gene of *Nicotiana tabacum*. Gene 148(2):195-202.

Haseloff J, Siemering K R, Prasher D C, Hodge S (1997) Removal of a cryptic intron and subcellular localization of green fluorescent protein are required to mark transgenic *Arabidopsis* plants brightly. Proceedings of the National Academy of Sciences of the United States of America 94: 2122-2127.

Hofgen R, Willmitzer L (1988) Storage of competent cells for *Agrobacterium* transformation. Nucleic Acids Research 16: 9877.

Hondred D, Walker J M, Mathews D E, Vierstra R D. 1999. Use of Ubiquitin Fusions to Augment Protein Expression in Transgenic Plants. Plant Physiol. 119(2):713-724.

Jefferson R A, Kavanagh T A, Bevan M W (1987) GUS fusions—Beta-glucuronidase as a sensitive and versatile gene fusion marker in higher-plants. Embo Journal 6: 3901-3907.

Kawalleck P, Somssich I E, Feldbrügge M, Hahlbrock K, Weisshaar B. 1993. Polyubiquitin gene expression and structural properties of the ubi4-2 gene in *Petroselinum crispum*. Plant Molecular Biology 21(4):673-684.

Leckie F, Devoto A, Delorenzo G (1994) Normalization of gus by luciferase activity from the same cell extract reduces transformation variability. Biotechniques 17: 52-3, 56-7.

Lepetit M, Ehling M, Gigot C, Hahne G (1991) An internal standard improves the reliability of transient expression studies in plant protoplasts. Plant Cell Reports 10: 401-405.

Lescot M, Dehais P, Thijs G, Marchal K, Moreau Y, Van de Peer Y, Rouze P, Rombauts S (2002) PlantCARE, a database of plant cis-acting regulatory elements and a portal to tools for in silico analysis of promoter sequences. Nucleic Acids Research 30: 325-327.

Mascarenhas D, Mettler I J, Pierce D A, Lowe H W. 1990. Intron-mediated enhancement of heterologous gene expression in maize. Plant Molecular Biology 15(6):913-920.

Murashige T, Skoog F (1962) A Revised Medium for Rapid Growth and Bio Assays with Tobacco Tissue Cultures. Physiologia Plantarum 15: 473-497.

Nakagawa T, Suzuki T, Murata S, Nakamura S, Hino T, Maeo K, Tabata R, Kawai T, Tanaka K, Niwa Y and others. 2007. Improved Gateway Binary Vectors: High-Performance Vectors for Creation of Fusion Constructs in Transgenic Analysis of Plants. Bioscience, Biotechnology, and Biochemistry 71(8):2095-2100.

Norris S R, Meyer S E, Callis J. 1993. The intron of *Arabidopsis thaliana* polyubiquitin genes is conserved in location and is a quantitative determinant of chimeric gene expression. Plant Molecular Biology 21(5):895-906.

Pelham H R H (1982) A regulatory upstream promoter element in Drosophila Hsp70 heat-shock gene. Cell 30: 517-528.

Rose A B, Beliakoff J A (2000) Intron-mediated enhancement of gene expression independent of unique intron sequences and splicing. Plant Physiology 22: 535-542.

Salamov A A, Solovyev V V (2000) Ab initio gene finding in *Drosophila* genomic DNA. Genome Research 10: 516-522.

Schledzewski K, Mendel R R (1994) Quantitative transient gene expression: comparison of the promoters for maize polyubiquitin1, rice actin1, maize-derived Emu and CaMV 35S in cells of barley, maize and tobacco. Transgenic Research 3: 249-255.

Sivamani E, Qu R. 2006. Expression Enhancement of a Rice Polyubiquitin Gene Promoter. Plant Molecular Biology 60(2):225-239.

Sivamani E, DeLong R K, Qu R D (2009) Protamine-mediated DNA coating remarkably improves bombardment transformation efficiency in plant cells. Plant Cell Reports 28: 213-221.

Tobias C M, Sarath G, Twigg P, Lindquist E, Pangilinan J, Penning B W, Barry K, McCann M C, Carpita N C, Lazo G R (2008) Comparative Genomics in Switchgrass Using 61,585 High-Quality Expressed Sequence Tags. The Plant Genome 1: 111-124.

Trick H N, Dinkins R D, Santarem E R, Samoyolov R D V, Meurer C, Walker D, Parrott W A, Finer J J, Collins G B (1997) Recent advances in soybean transformation. Plant tissue culture and biotechnology 3: 9-26.

Varshaysky A (2005) Ubiquitin fusion technique and related methods. Methods in Enzymology 399: 777-799.

Walker J M, Vierstra R D (2007) A ubiquitin-based vector for the co-ordinated synthesis of multiple proteins in plants. Plant Biotechnology Journal 5: 413-421.

Wang J, Jiang J, Oard J H. 2000. Structure, expression and promoter activity of two polyubiquitin genes from rice (*Oryza sativa* L.). Plant Science 156(2):201-211.

Wei H, Wang M-L, Moore P H, Albert H H. 2003. Comparative expression analysis of two sugarcane polyubiquitin promoters and flanking sequences in transgenic plants. Journal of Plant Physiology 160(10):1241-1251.

Xie Q-E, Yan X-L, Liao X-Y, Li X (2009) The Arsenic Hyperaccumulator Fern *Pteris vittata* L. Environmental Science & Technology 43: 8488-8495.

We claim:

1. An isolated nucleic acid molecule comprising:
   a) a nucleotide sequence comprising the sequence set forth in SEQ ID NO: 2 or a nucleotide sequence fully complementary thereto; or
   b) a nucleotide sequence comprising nucleotides 1 to 692 of SEQ ID NO: 2 or a sequence fully complementary thereto;
   wherein said isolated nucleic acid molecule further comprises a label selected from the group consisting of a radioactive label, enzyme label, chemiluminescent label, fluorescent label, and magnetic label.

2. A DNA construct comprising a heterologous nucleotide sequence of interest operably linked to a nucleotide sequence comprising:
   a) SEQ ID NO: 2; or
   b) a nucleotide sequence comprising nucleotides 1 to 692 of SEQ ID NO: 2.

3. A vector comprising a DNA construct comprising a heterologous nucleotide sequence of interest operably linked to a nucleotide sequence comprising:
   a) SEQ ID NO: 2; or
   b) a nucleotide sequence comprising nucleotides 1 to 692 of SEQ ID NO: 2.

4. A plant cell having stably incorporated into its genome a DNA construct comprising a heterologous nucleotide sequence of interest operably linked to a nucleotide sequence comprising:
   a) SEQ ID NO: 2; or
   b) a nucleotide sequence comprising nucleotides 1 to 692 of SEQ ID NO: 2.

5. The plant cell of claim 4, wherein said plant cell is from a monocot.

6. The plant cell of claim 4, wherein said plant cell is from a dicot.

7. The plant cell of claim 4, wherein said plant cell is from a fern.

8. A plant having stably incorporated into its genome a DNA construct comprising a heterologous nucleotide sequence of interest operably linked to a nucleotide sequence comprising:
   a) SEQ ID NO: 2; or
   b) a nucleotide sequence comprising nucleotides 1 to 692 of SEQ ID NO: 2.

9. The plant of claim 8, wherein said plant is a monocot.

10. The plant of claim 8, wherein said plant is a dicot.

11. The plant of claim 8, wherein the heterologous nucleotide sequence of interest encodes a gene product that confers herbicide, salt, heat, cold, flood, drought, pathogen, or insect resistance.

12. A fern having stably incorporated into its genome a DNA construct comprising a heterologous nucleotide sequence of interest operably linked to a nucleotide sequence comprising:
  a) SEQ ID NO:2; or
  b) a nucleotide sequence comprising nucleotides 1 to 692 of SEQ ID NO: 2.

13. The fern of claim 12, wherein the heterologous nucleotide sequence of interest encodes a gene product that confers herbicide, salt, heat, cold, flood, drought, pathogen, or insect resistance.

14. A transgenic seed comprising a DNA construct comprising a heterologus nucleotide sequence of interest operably linked to a nucleotide sequence comprising:
  a) SEQ ID NO: 2; or
  b) a nucleotide sequence comprising a nucleotides 1 to 692 of SEQ ID NO: 2.

15. A transgenic spore, gametophyte or zygote comprising a DNA construct comprising a heterologous nucleotide sequence of interest operably linked to a nucleotide sequence comprising:
  a) SEQ ID NO: 2; or
  b) a nucleotide sequence comprising nucleotides 1 to 692 of SEQ ID NO: 2.

16. A method for expressing a nucleotide sequence in a plant, said method comprising introducing into a plant a DNA construct, said DNA construct comprising a promoter operably linked to a heterologous nucleotide sequence of interest, wherein said promoter comprises a nucleotide sequence selected from the group consisting of:
  a) a nucleotide sequence comprising the sequence set forth in SEQ ID NO: 2; and
  b) a nucleotide sequence comprising nucleotides 1 to 692 of SEQ ID NO: 2.

17. The method of claim 16, wherein said plant is a dicot.

18. The method of claim 16, wherein said plant is a monocot.

19. The method of claim 16, wherein said plant is a fern.

20. The method of claim 16, wherein the heterologous nucleotide sequence encodes a gene product that confers herbicide, salt, heat, cold, flood, drought, pathogen, or insect resistance.

21. A method for introducing a nucleotide sequence into a plant cell comprising introducing into a plant cell a DNA construct comprising a promoter operably linked to a heterologous nucleotide sequence of interest, wherein said promoter comprises a nucleotide sequence selected from the group consisting of:
  a) a nucleotide sequence comprising the sequence set forth in SEQ ID NO: 2; and
  b) a nucleotide sequence comprising nucleotides 1 to 692 of SEQ ID NO: 2.

22. The method of claim 21, wherein said plant cell is from a monocot.

23. The method of claim 21, wherein said plant cell is from a dicot.

24. The isolated nucleic acid molecule according to claim 1, wherein said isolated nucleic acid molecule comprises SEQ ID NO: 2.

25. The isolated nucleic acid molecule according to claim 1, wherein said nucleic acid molecule comprises nucleotides 1 to 692 of SEQ ID NO: 2 or a nucleotide sequence fully complementary thereto.

* * * * *

UNITED STATES PATENT AND TRADEMARK OFFICE
CERTIFICATE OF CORRECTION

PATENT NO.        : 8,604,276 B2                                          Page 1 of 1
APPLICATION NO.   : 12/797248
DATED             : December 10, 2013
INVENTOR(S)       : C. Neal Stewart and David George James Mann It is certified that error appears in the above-identified patent and that said Letters Patent is hereby corrected as shown below:

In the Specification

Column 14,
Line 1, "*J. Bacteria*" should read --*J. Bacteriol.*--.

Column 15,
Line 24, "(*Medicago saliva*)" should read --(*Medicago sativa*)--.
Line 25, "(*Sectile cereale*)" should read --(*Secale cereale*)--.

Column 24,
Line 21, "(www.agroniastate.edu/ptf/protocol/Embryo%20bb.pdf)" should read
    --(www.agron.iastate.edu/ptf/protocol/Embryo%20bb.pdf)--.
Lines 27-28, "4-Methylumbeiliferyl" should read --4-Methylumbelliferyl--.

Column 26,
Line 8, "PvUib1" should read --PvUbi1--.

Column 27,
Line 38, "(Varshaysky," should read --(Varshavsky,--.

Column 32,
Line 32, "Varshaysky" should read --Varshavsky--.

Signed and Sealed this
Twenty-eighth Day of October, 2014

Michelle K. Lee
*Deputy Director of the United States Patent and Trademark Office*

SEQUENCE LISTING

```
<160> NUMBER OF SEQ ID NOS: 47

<210> SEQ ID NO 1
<211> LENGTH: 2036
<212> TYPE: DNA
<213> ORGANISM: Panicum virgatum

<400> SEQUENCE: 1
ccactggaga ggggcacaca cgtcagtgtt tggtttccac tagcacgagt agcgcaatca      60
gaaaattttc aatgcatgaa gtactaaacg aagtttattt agaaattttt ttaagaaatg     120
agtgtaattt tttgcgacga atttaatgac ataattaat cgatgattgc ctacagtaat      180
gctacagtaa ccaacctcta atcatgcgtc gaatgcgtca ttagattcgt ctcgcaaaat     240
agcacaagaa ttatgaaatt aattttacaa actattttta tttaatacta ataattaact    300
```

```
gtcaaagttt gtgctactcg caagagtagc gcgaaccaaa cacggcctgg aggagcacgg    360
taacggcgtc gacaaactaa cggccaccac ccgccaacgc aaaggagacg gatgagagtt    420
gacttcttga cggttctcca cccctctgtc tctctgtcac tgggcsctgg gtccccctct    480
cgaaagttcc tctggccgaa attgcgcggc ggagacgagg cgggcggaac cgtcacggca    540
gaggattcct tccccaccct gcctggcccg gccatatata aacagccacc gcccctcccc    600
gttcsccatc gcgtctcgtc tcgtgttgtt cccagaacac aaccaaaatc caaatcctcc    660
tcctcctccc gagcctcgtc gatccctcac ccgcttcaag gtacggcgat cctcctctcc    720
cttctcccct cgatcgatta tgcgtgttcc gtttccgttt ccgatcgagc gaatcgatgg    780
ttaggaccca tggggaccc atggggtgtc gtgtggtggt ctggtttgat ccgcgatatt    840
tctccgttcg tagtgtagat ctgatcgaat ccctggtgaa atcgttgatc gtgctattcg    900
tgtgagggtt cttaggtttg gagttgtgga ggtagttctg atcggtttgt aggtgagatt    960
ttccccatga ttttgcttgg ctcgtttgtc ttggttagat tagatctgcc cgcattttgt   1020
tcgatatttc tgatgcagat atgatgaata atttcgtcct tgtatcccgc gtccgtatgt   1080
gtattaagtt tgcaggtgct agttaggttt ttcctactga tttgtcttat ccattctgtt   1140
tagcttgcaa ggtttggtaa tggtccggca tgtttgtctc tatagattag agtagaataa   1200
gattatctca acaagctgtt ggcttatcaa ttttggatct gcatgtgttt cgcatctata   1260
tctttgcaat taagatggta gatggacata tgctcctgtt gagttgatgt tgtacctttt   1320
acctgaggtc tgaggaacat gcatcctcct gctactttgt gcttatacag atcatcaaga   1380
ttatgcagct aatattcgat cagtttctag tatctacatg gtaaacttgc atgcacttgc   1440
tacttatttt tgatatactt ggatgataac atatgctgct ggttgattcc tacctacatg   1500
atgaacattt tacaggccat tagtgtctgt ctgtatgtgt tgttcctgtt tgcttcagtc   1560
tatttctgtt tcattcctag tttattggtt ctctgctaga tacttaccct gctgggctta   1620
gttatcatct tatctcgaat gcattttcat gtttatagat gaatatacac tcagataggt   1680
gtagatgtat gctactgttt ctctacgttg ctgtaggttt tacctgtggc aactgcatac   1740
tcctgttgct tcgctagata tgtatgtgct tatatagatt aagatatgtg tgatggttct   1800
ttagtatatc tgatgatcat gtatgctctt ttaacttctt gctacacttg gtaacatgct   1860
gtgatgctgt ttgttgattc tgtagcacta ccaatgatga ccttatctct ctttgtatat   1920
gatgtttctg tttgtttgag gcttgtgtta ctgctagtta cttaccctgt tgcctggcta   1980
atcttctgca gatgcagatc ttcgttaaga ccctcaccgg caagaccatc acctc        2036
```

<210> SEQ ID NO 2
<211> LENGTH: 1906
<212> TYPE: DNA
<213> ORGANISM: Panicum virgatum

<400> SEQUENCE: 2

```
gaagccaact aaacaagacc ataaccatgg tgacatttga catagttgtt tactacttgc     60
ttgagcccca cccttgctta tcggttgaac attacaagat acactgcggg tggcctaagg    120
cacaccgtcc gaaaccggca aaccaagcct gatcgccgaa atccaaaatc actaccggca    180
atctctaaag tttatttcat ccttatatga cgaggaaaga aagaagaga gaaataatat    240 cttaacttct aaatcagtcg cgtcaacttt ctcggctaag aaagtgagca ctatcatttc    300
ggagaccatg tcatgagtgc cgacttgcca tatcttatta tattcttatt tatttaatta    360
taatcccatt gcaatacgtc tattctatca tggcctgcca ctaacgctcc gtctaacgtc    420
```

```
gttaagccat tgtcataagc ggctgctcaa aactcttccc ggtggaggcg aggcgttaac    480
ggcgtctaca aatctaacgg ccaccaacca tccagccgcc tctcgaaagc tccgctccga    540
tcgcggaaat tgcgtggcgg agacgagcgg gctcctctca cacggcccgg aaccgtcacg    600
gcacgggtgg gggattcctt ccccaaccct ccccacctct cctcccccg tcgcagccca    660 taaatacagg gccctccgcg cctcttccca caatctcaca tcgtctcatc gttcggagcg    720
cacaaccccc gggttccaaa tccaaattgc tcttctcgcg accctcggcg atccttcccc    780
cgcttcaagg tacggcgatc gtctccccg tcctcttgcc ccatctcctc gctcggcgtg    840
gtttggtggt tctgcttggt ctgtggctag gaactaggct gaggcgttga cgaaatcatg    900
ctagatccgc gtgtttcctg atcgtgggtg gctgggaggt ggggttttcg tgtagatctg    960
atcggttccg ctgtttatcc tgtcatgctc atgtgatttg tggggatttt aggtcgtttg   1020
tccgggaatc gtggggttgc ttctaggctt ttcgtagatg agatcgttct cacgatctgc   1080
tgggtcgctg cctaggttca gctaggtctg ccctgttttt gggttcgttt tcgggatctg   1140
tacgtgcatc tattatctgg ttcgatggtg ctagctagga acaaacaact gattcgtccg   1200
atcgattgtt ttgttgccat gtgcaaggtt aggtcgttat ctgattgctg tagatcagag   1260
tagaataaga tcatcacaag ctagctcttg ggcttattat gaatctgcgt ttgttgcatg   1320
attaagatga ttatgctttt tcttatgctg ccgtttgtat atgatgcggt agcttttaac   1380
tgaatagcac acctttcctg tttagttaga ttagattaga ttgcatgata gatgaggata   1440
tatgctgcta catcagtttg atgattctct ggtacctcat aatcaactag ctcatgtgct   1500
taaattgaaa ctgcatgtgc cacatgatta agatgctaag attggtgaag atatatacgc   1560
tgctgttcct ataggatcct gtagcttta cctggtcaac atgcatcgtc ctgttatgga   1620
tagatatgca tgatagatga agatatgtac tgctacaatt tgatgattct tttgtgcacc   1680
tgatgatcat gcatgctctt tgcccttact ttgatatact tggatgatgg catgcttagt   1740
actaatgatg tgatgaacac acatgacctg ttggtatgaa tatgatgttg ctgtttgctt   1800
gtgatgagtt ctgtttgttt actgctaggc acttaccctg ttgtctggtt ctcttttgca   1860
gatgcagatc tttgtgaaga ccctcaccgg caagaccatc accctc                  1906
```

```
<210> SEQ ID NO 3
<211> LENGTH: 15
<212> TYPE: PRT
<213> ORGANISM: Panicum virgatum

<400> SEQUENCE: 3

Met Gln Ile Phe Val Lys Thr Leu Thr Gly Lys Thr Ile Thr Leu
1               5                   10                  15

<210> SEQ ID NO 4
<211> LENGTH: 22
<212> TYPE: DNA
<213> ORGANISM: Artificial Sequence
<220> FEATURE:
<223> OTHER INFORMATION: PvUbi1-F1 primer

<400> SEQUENCE: 4
ccactggaga ggggcacaca cg                                              22

<210> SEQ ID NO 5
<211> LENGTH: 26
<212> TYPE: DNA
<213> ORGANISM: Artificial Sequence
<220> FEATURE:
```

```
<223> OTHER INFORMATION: PvUbi1-R1 primer

<400> SEQUENCE: 5
ctgcagaaga ttagccaggc aacagg                                          26

<210> SEQ ID NO 6
<211> LENGTH: 22
<212> TYPE: DNA
<213> ORGANISM: Artificial Sequence
<220> FEATURE:
<223> OTHER INFORMATION: PvUbi1-F1 primer

<400> SEQUENCE: 6
ccactggaga ggggcacaca cg                                              22

<210> SEQ ID NO 7
<211> LENGTH: 28
<212> TYPE: DNA
<213> ORGANISM: Artificial Sequence
<220> FEATURE:
<223> OTHER INFORMATION: PvUbi1+3-R1 primer

<400> SEQUENCE: 7
gatctgcatc tgcagaagat tagccagg                                        28

<210> SEQ ID NO 8
<211> LENGTH: 33
<212> TYPE: DNA
<213> ORGANISM: Artificial Sequence
<220> FEATURE:
<223> OTHER INFORMATION: PvUbi1-F2 primer

<400> SEQUENCE: 8
ccactggaga ggggcacaca cgtcagtgtt tgg                                  33

<210> SEQ ID NO 9
<211> LENGTH: 33
<212> TYPE: DNA
<213> ORGANISM: Artificial Sequence
<220> FEATURE:
<223> OTHER INFORMATION: PvUbi1+9-R1 primer

<400> SEQUENCE: 9
ggtgagggtc ttaacgaaga tctgcatctg cag                                  33

<210> SEQ ID NO 10
<211> LENGTH: 20
<212> TYPE: DNA
<213> ORGANISM: Artificial Sequence
<220> FEATURE:
<223> OTHER INFORMATION: PvUbi1-3'R primer

<400> SEQUENCE: 10
cagcttggat gaccaatggc                                                 20

<210> SEQ ID NO 11
<211> LENGTH: 18
<212> TYPE: DNA
<213> ORGANISM: Artificial Sequence
<220> FEATURE:
<223> OTHER INFORMATION: PvUbi1-3'F3 primer

<400> SEQUENCE: 11
atttagtgct ccgcctcc                                                   18

<210> SEQ ID NO 12
```

```
<211> LENGTH: 24
<212> TYPE: DNA
<213> ORGANISM: Artificial Sequence
<220> FEATURE:
<223> OTHER INFORMATION: PvUbi2-R2 primer

<400> SEQUENCE: 12
gtgagggtct tcacaaagat ctgc                                              24

<210> SEQ ID NO 13
<211> LENGTH: 22
<212> TYPE: DNA
<213> ORGANISM: Artificial Sequence
<220> FEATURE:
<223> OTHER INFORMATION: PvUbi2-5'F primer

<400> SEQUENCE: 13
ctcacatcgt ctcatcgttc gg                                                22

<210> SEQ ID NO 14
<211> LENGTH: 18
<212> TYPE: DNA
<213> ORGANISM: Artificial Sequence
<220> FEATURE:
<223> OTHER INFORMATION: PvUbi1-RT-F4 primer

<400> SEQUENCE: 14
ttggtgctcc gcctgaga                                                     18

<210> SEQ ID NO 15
<211> LENGTH: 20
<212> TYPE: DNA
<213> ORGANISM: Artificial Sequence
<220> FEATURE:
<223> OTHER INFORMATION: PvUbi1-RT-R4 primer

<400> SEQUENCE: 15
cctggatctt ggccttcaca                                                   20

<210> SEQ ID NO 16
<211> LENGTH: 21
<212> TYPE: DNA
<213> ORGANISM: Artificial Sequence
<220> FEATURE:
<223> OTHER INFORMATION: PvUbi2-RT-F2 primer

<400> SEQUENCE: 16
aagtatatgc gtcatttggc g                                                 21

<210> SEQ ID NO 17
<211> LENGTH: 19
<212> TYPE: DNA
<213> ORGANISM: Artificial Sequence
<220> FEATURE:
<223> OTHER INFORMATION: PvUbi2-RT-R2 primer

<400> SEQUENCE: 17
atactgctgc accaccaca                                                    19

<210> SEQ ID NO 18
<211> LENGTH: 20
<212> TYPE: DNA
<213> ORGANISM: Artificial Sequence
<220> FEATURE:
<223> OTHER INFORMATION: PvAct-RT-F1 primer

<400> SEQUENCE: 18
```

```
caagatttgg agatcccgtg                                           20

<210> SEQ ID NO 19
<211> LENGTH: 19
<212> TYPE: DNA
<213> ORGANISM: Artificial Sequence
<220> FEATURE:
<223> OTHER INFORMATION: PvAct-RT-R1 primer

<400> SEQUENCE: 19
aatgctccac ggcgaacag                                            19

<210> SEQ ID NO 20
<211> LENGTH: 22
<212> TYPE: DNA
<213> ORGANISM: Artificial Sequence
<220> FEATURE:
<223> OTHER INFORMATION: 35S-F primer

<400> SEQUENCE: 20
agattagcct tttcaatttc ag                                        22

<210> SEQ ID NO 21
<211> LENGTH: 20
<212> TYPE: DNA
<213> ORGANISM: Artificial Sequence
<220> FEATURE:
<223> OTHER INFORMATION: 35S-R primer

<400> SEQUENCE: 21
cgtgttctct ccaaatgaaa                                           20

<210> SEQ ID NO 22
<211> LENGTH: 22
<212> TYPE: DNA
<213> ORGANISM: Artificial Sequence
<220> FEATURE:
<223> OTHER INFORMATION: d35S-F primer

<400> SEQUENCE: 22
ggtcaacatg gtggagcacg ac                                        22

<210> SEQ ID NO 23
<211> LENGTH: 23
<212> TYPE: DNA
<213> ORGANISM: Artificial Sequence
<220> FEATURE:
<223> OTHER INFORMATION: d35S-R primer

<400> SEQUENCE: 23
gggatcctct agagtcgagg tcc                                       23

<210> SEQ ID NO 24
<211> LENGTH: 20
<212> TYPE: DNA
<213> ORGANISM: Artificial Sequence
<220> FEATURE:
<223> OTHER INFORMATION: OsAct1-F primer

<400> SEQUENCE: 24
ctcgaggtca ttcatatgct                                           20

<210> SEQ ID NO 25
<211> LENGTH: 20
<212> TYPE: DNA
<213> ORGANISM: Artificial Sequence
<220> FEATURE:
```

<223> OTHER INFORMATION: OsAct1-R primer

<400> SEQUENCE: 25
tctacctaca aaaaagctcc                                               20

<210> SEQ ID NO 26
<211> LENGTH: 20
<212> TYPE: DNA
<213> ORGANISM: Artificial Sequence
<220> FEATURE:
<223> OTHER INFORMATION: ZmUbi1-F primer

<400> SEQUENCE: 26
tgcagtgcag cgtgacccgg                                               20

<210> SEQ ID NO 27
<211> LENGTH: 26
<212> TYPE: DNA
<213> ORGANISM: Artificial Sequence
<220> FEATURE:
<223> OTHER INFORMATION: ZmUbi1-R primer

<400> SEQUENCE: 27
tgcagaagta acaccaaaca acaggg                                        26

<210> SEQ ID NO 28
<211> LENGTH: 22
<212> TYPE: DNA
<213> ORGANISM: Artificial Sequence
<220> FEATURE:
<223> OTHER INFORMATION: PvUbi1-F primer

<400> SEQUENCE: 28
ccactggaga ggggcacaca cg                                            22

<210> SEQ ID NO 29
<211> LENGTH: 26
<212> TYPE: DNA
<213> ORGANISM: Artificial Sequence
<220> FEATURE:
<223> OTHER INFORMATION: PvUbi1-R primer

<400> SEQUENCE: 29
ctgcagaaga ttagccaggc aacagg                                        26

<210> SEQ ID NO 30
<211> LENGTH: 22
<212> TYPE: DNA
<213> ORGANISM: Artificial Sequence
<220> FEATURE:
<223> OTHER INFORMATION: PvUbi1-F primer

<400> SEQUENCE: 30
ccactggaga ggggcacaca cg                                            22

<210> SEQ ID NO 31
<211> LENGTH: 28
<212> TYPE: DNA
<213> ORGANISM: Artificial Sequence
<220> FEATURE:
<223> OTHER INFORMATION: PvUbi1+3-R primer

<400> SEQUENCE: 31
gatctgcatc tgcagaagat tagccagg                                      28

<210> SEQ ID NO 32

```
<211> LENGTH: 28
<212> TYPE: DNA
<213> ORGANISM: Artificial Sequence
<220> FEATURE:
<223> OTHER INFORMATION: PvUbi1+9-F primer

<400> SEQUENCE: 32
ccactggaga ggggcacaca cgtcagtg                                              28

<210> SEQ ID NO 33
<211> LENGTH: 33
<212> TYPE: DNA
<213> ORGANISM: Artificial Sequence
<220> FEATURE:
<223> OTHER INFORMATION: PvUbi1+9-R primer

<400> SEQUENCE: 33
ggtgagggtc ttaacgaaga tctgcatctg cag                                        33

<210> SEQ ID NO 34
<211> LENGTH: 32
<212> TYPE: DNA
<213> ORGANISM: Artificial Sequence
<220> FEATURE:
<223> OTHER INFORMATION: PvUbi2-F primer

<400> SEQUENCE: 34
gaagccaact aaacaagacc ataaccatgg tg                                         32

<210> SEQ ID NO 35
<211> LENGTH: 26
<212> TYPE: DNA
<213> ORGANISM: Artificial Sequence
<220> FEATURE:
<223> OTHER INFORMATION: PvUbi2-R primer

<400> SEQUENCE: 35
ctgcaaaaga gaaccagaca acaggg                                                26

<210> SEQ ID NO 36
<211> LENGTH: 32
<212> TYPE: DNA
<213> ORGANISM: Artificial Sequence
<220> FEATURE:
<223> OTHER INFORMATION: PvUbi2-F primer

<400> SEQUENCE: 36
gaagccaact aaacaagacc ataaccatgg tg                                         32

<210> SEQ ID NO 37
<211> LENGTH: 28
<212> TYPE: DNA
<213> ORGANISM: Artificial Sequence
<220> FEATURE:
<223> OTHER INFORMATION: PvUbi2+3-R primer

<400> SEQUENCE: 37
gatctgcatc tgcaaaagag aaccagac                                              28

<210> SEQ ID NO 38
<211> LENGTH: 32
<212> TYPE: DNA
<213> ORGANISM: Artificial Sequence
<220> FEATURE:
<223> OTHER INFORMATION: PvUbi2-F primer

<400> SEQUENCE: 38
```

```
gaagccaact aaacaagacc ataaccatgg tg                                32
```

<210> SEQ ID NO 39
<211> LENGTH: 28
<212> TYPE: DNA
<213> ORGANISM: Artificial Sequence
<220> FEATURE:
<223> OTHER INFORMATION: PvUbi2+9-R primer

<400> SEQUENCE: 39

```
ggtgagggtc ttcacaaaga tctgcatc                                    28
```

<210> SEQ ID NO 40
<211> LENGTH: 20
<212> TYPE: PRT
<213> ORGANISM: Artificial Sequence
<220> FEATURE:
<223> OTHER INFORMATION: primer

<400> SEQUENCE: 40

Thr Asx Ala Cys Tyr Gly Gly Met Ala Ala Gly Ala Cys Asx Ala Thr
 1               5                  10                  15

His Ala Cys Tyr
            20

<210> SEQ ID NO 41
<211> LENGTH: 20
<212> TYPE: PRT
<213> ORGANISM: Artificial Sequence
<220> FEATURE:
<223> OTHER INFORMATION: primer

<400> SEQUENCE: 41

Thr Cys Cys Thr Thr Tyr Thr Gly Arg Ala Thr Gly Thr Thr Arg Thr
 1               5                  10                  15

Ala Arg Thr Cys
            20

<210> SEQ ID NO 42
<211> LENGTH: 12
<212> TYPE: DNA
<213> ORGANISM: Panicum virgatum

<400> SEQUENCE: 42

```
attaatttta ca                                                     12
```

<210> SEQ ID NO 43
<211> LENGTH: 14
<212> TYPE: DNA
<213> ORGANISM: Drosophila melanogaster
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 43

```
cnngaanntt cnng                                                   14
```

<210> SEQ ID NO 44

```
<211> LENGTH: 27
<212> TYPE: DNA
<213> ORGANISM: Artificial sequence
<220> FEATURE:
<223> OTHER INFORMATION: Nucleotides encoding the first 9 amino acids
      of PvUbi1 ubiquitin

<400> SEQUENCE: 44
atgcagatct cgttaagac cctcacc                                          27

<210> SEQ ID NO 45
<211> LENGTH: 9
<212> TYPE: DNA
<213> ORGANISM: Artificial sequence
<220> FEATURE:
<223> OTHER INFORMATION: Nucleotides encoding the first 3 amino acids
      of PvUbi1 and PvUbi2 ubiquitin

<400> SEQUENCE: 45 atgcagatc                                                              9

<210> SEQ ID NO 46
<211> LENGTH: 27
<212> TYPE: DNA
<213> ORGANISM: Artificial sequence
<220> FEATURE:
<223> OTHER INFORMATION: Nucleotides encoding the first 9 amino acids
      of PvUbi1 ubiquitin

<400> SEQUENCE: 46
atgcagatct cgttaagac cctcacc                                          27

<210> SEQ ID NO 47
<211> LENGTH: 27
<212> TYPE: DNA
<213> ORGANISM: Artificial sequence
<220> FEATURE:
<223> OTHER INFORMATION: Nucleotides encoding the first 9 amino acids
      of PvUbi2 ubiquitin

<400> SEQUENCE: 47
atgcagatct ttgtgaagac cctcacc                                         27
```